United States Patent
Boudjelal et al.

(10) Patent No.: US 10,639,382 B2
(45) Date of Patent: May 5, 2020

(54) METHOD FOR TREATING LEUKEMIA

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventors: Mohamed Boudjelal, Riyadh (SA); Atef Nehdi, Riyadh (SA); Ahmed Sulaiman Alaskar, Riyadh (SA); Imadul Islam, Riyadh (SA); Hajar Mohammed Alzahrani, Riyadh (SA)

(73) Assignees: National Guard Health Affairs, Riyadh (SA); King Saud bin Abdulaziz University for Health Services, Riyadh (SA); King Abdullah International Medical Research Center, Riyadh (SA)

( * ) Notice: Subject to any disclaimer, the term of this patent is extended or adjusted under 35 U.S.C. 154(b) by 177 days.

(21) Appl. No.: 15/487,050

(22) Filed: Apr. 13, 2017

(65) Prior Publication Data

US 2018/0296692 A1    Oct. 18, 2018

(51) Int. Cl.
| | |
|---|---|
| *A61K 47/68* | (2017.01) |
| *A61K 31/137* | (2006.01) |
| *A61K 31/198* | (2006.01) |
| *A61K 31/704* | (2006.01) |
| *A61K 31/5513* | (2006.01) |

(52) U.S. Cl.
CPC ........ *A61K 47/6851* (2017.08); *A61K 31/137* (2013.01); *A61K 31/198* (2013.01); *A61K 31/5513* (2013.01); *A61K 31/704* (2013.01); *A61K 47/6803* (2017.08); *A61K 47/6867* (2017.08)

(58) Field of Classification Search
CPC ............... A61K 47/6851; A61K 47/68; A61K 47/6867; A61K 31/137; A61K 31/198; A61K 31/704

USPC ........................................... 424/179.1, 178.1
See application file for complete search history.

(56) References Cited

U.S. PATENT DOCUMENTS

2006/0127407 A1   6/2006  Chen et al.
2008/0125415 A1   5/2008  Roth et al.

FOREIGN PATENT DOCUMENTS

DE         3812605       6/1990
WO      2015/013169      1/2015

OTHER PUBLICATIONS

Strati et al. (Cancer, 2014, 120: 373-80).*
Gholam Reza Shariati et al., "Expression Changes of Serotonin Receptor gene Subtype 5HT3a in Peripheral Blood Mononuclear Cells from Schizophrenic Patients Treated with Haloperidol and Olanzapin," Iranian Journal of Allergy, Asthma and Immunology, Sep. 2009, vol. 8, No. 3, pp. 135-139.
Robert J. Benschop et al., "Psychobiological factors related to human natural killer cell activity and hormonal modulation of NK cells in vitro," Life Sciences, 1993, vol. 52, No. 23.
L.D. Johnson et al., "The Effects of Isoproterenol and Cyclic Adenosine 3',5'-Phosphate on Phytohemagglutinin-stimulated DNA Synthesis in Lymphocytes Obtained from Patients with Chronic Lymphocytic Leukemia," Cancer Research, Nov. 1970, vol. 30, pp. 2718-2723.

* cited by examiner

*Primary Examiner* — Yan Xiao
(74) *Attorney, Agent, or Firm* — Oblon, McClelland, Maier & Neustadt, L.L.P.

(57) ABSTRACT

The present disclosure relates to methods of reducing the number of abnormal PBMC cells in a leukemia patient. The methods may include administering an effective amount of a drug, which may not be indicated for leukemia, or an antibody-drug conjugate. The antibody-drug conjugate includes an antibody selected from the group consisting of an anti-$\alpha_2$-adrenoreceptor antibody, an anti-$\beta$ adrenoceptor antibody, an anti-trace amine-associated receptor 1 antibody, an anti-dopamine receptor antibody, and an anti-serotonin receptor antibody; a drug selected from the group consisting of isoproterenol, methyldopa, olanzapine, and a derivative thereof; and a linker that conjugates the antibody and the drug.

12 Claims, 33 Drawing Sheets

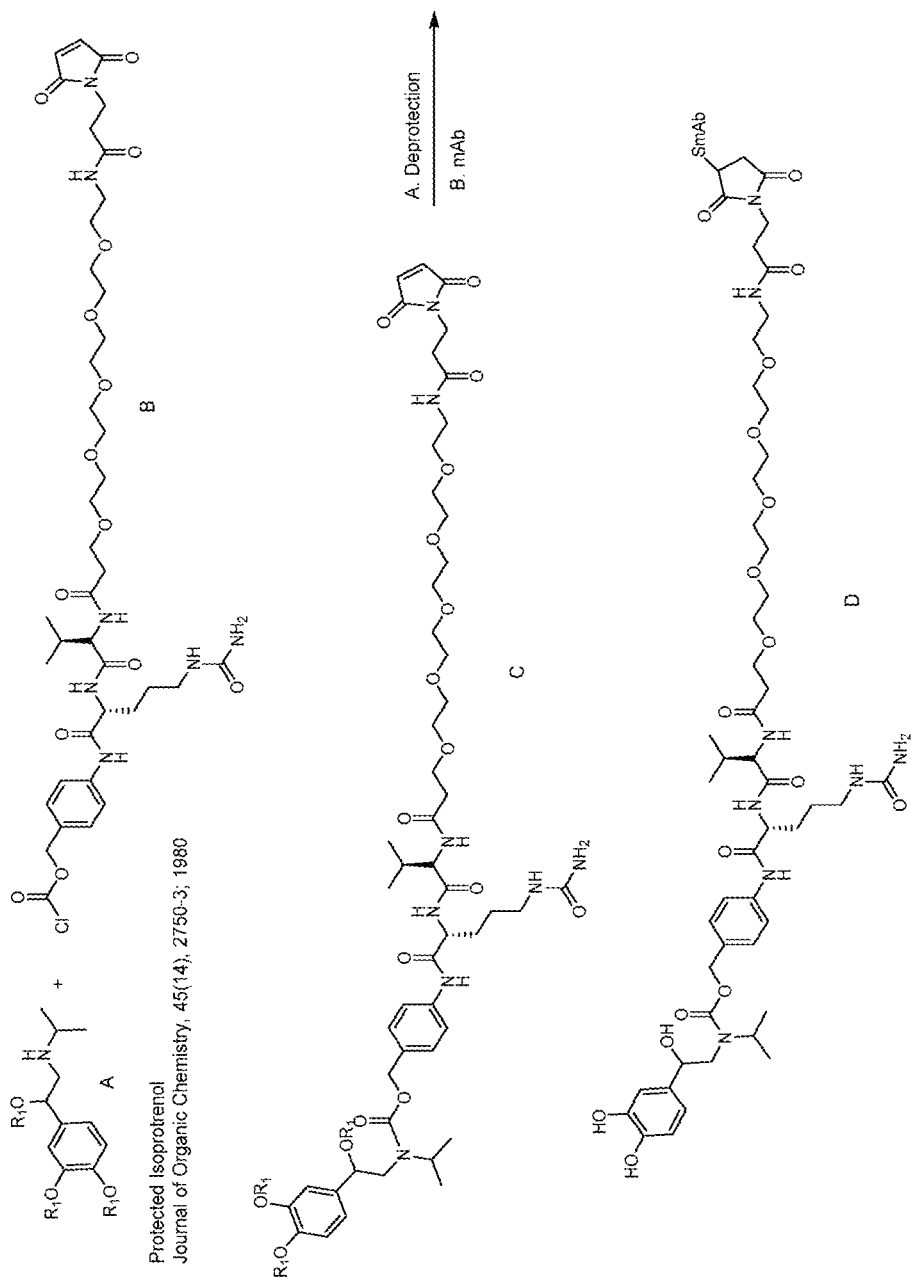

METHOD FOR TREATING LEUKEMIA

BACKGROUND OF THE INVENTION

Technical Field

The present disclosure relates to methods of treating leukemia patients with methyldopa, olanzapine, and isoproterenol. The present disclosure also relates to an anti-$\alpha_2$ adrenoceptor antibody, an anti-β adrenoceptor antibody, an anti-trace amine-associated receptor 1 antibody, an anti-dopamine receptor antibody, or an anti-serotonin receptor antibody and antibody-drug conjugates of the antibodies. The present disclosure further relates to methods of delivering such antibodies and antibody-drug conjugates for the treatment of leukemia. Further, the present disclosure describes employing freshly gathered primary cells for compound screening for diseases.

DESCRIPTION OF THE RELATED ART

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The search of new drugs is ongoing and challenging for all diseases, including cancer which is becoming the world-wide number one killer of patients. As a sub-category of cancer, leukemia diagnoses are wide-spread and leukemia often may develop a resistance to existing drugs. With this in mind, developing and discovery of new medication for leukemia and other cancers is an objective of many researchers around the world.

Leukemia is a malignant progressive disease in which the bone marrow and other blood-forming organs produce increased numbers of immature or abnormal leukocytes. These abnormal leukocytes suppress the production of normal blood cells, leading to anemia and other symptoms. Leukemia presents in patients in several forms including acute lymphoblastic leukemia (ALL), acute myeloid leukemia (AML), chronic lymphocytic leukemia (CLL) and chronic myeloid leukemia (CML), as well as a number of less common types. Leukemia and lymphoma both belong to a broader group of tumors that affect the blood, bone marrow, and lymphoid system, known as tumors of the hematopoietic and lymphoid tissues.

Treatment may involve a combination of chemotherapy, radiation therapy, targeted therapy, and bone marrow transplant, in addition to supportive care and palliative care as needed. The success of treatment depends on the type of leukemia and the age of the person. Outcomes have improved in the developed world. The average five-year survival rate is 57% in the United States. In children under 15, the five-year survival rate is greater than 60% to 85%, depending on the type of leukemia. In children with acute leukemia who are cancer-free after five years, the cancer is unlikely to return. Roughly 90% of all leukemias are diagnosed in adults, with AML and CLL being most common in adults.

A form of targeted therapy in use is antibody-drug conjugates (ADCs). ADCs combine the specificity and targeting of high affinity antibodies with the cytotoxicity of a therapeutic agent, such as cytotoxic agents, biological response modifiers, enzymes, apoptosis-inducing agents, and radioisotopes. Release of therapeutic agents from the antibody can require trafficking and localization of the antibody-drug conjugate to lysosomes.

In view of the forgoing, an objective of the present invention is to provide an ADC for the targeted therapy of leukemia. It is a further objective to repurpose off-patent drugs for leukemia.

BRIEF SUMMARY OF THE INVENTION

A first aspect of the disclosure relates to a method for reducing a number of abnormal peripheral blood mononuclear cells (PBMC) in a chronic myelogenous leukemia patient, the method comprising administering an effective amount of isoproterenol to the chronic myelogenous leukemia patient, thereby reducing the number of abnormal PBMC in the chronic myelogenous leukemia patient.

In some implementations of the method, the number of abnormal PBMC is reduced by 5% to 80% relative to an initial number of abnormal PBMC in the chronic myelogenous leukemia patient prior to administering the effective amount of isoproterenol.

In some implementations of the method, the effective amount of isoproterenol is in range of 1-100 mg/kg.

In some implementations of the method, the method further comprises administering an effective amount of doxorubicin to the chronic myelogenous leukemia patient together with the administering of the effective amount of isoproterenol.

In some implementations of the method, the effective amount of doxorubicin is in a range of 1-100 mg/kg.

A second aspect of the disclosure relates to a method for reducing a number of abnormal PBMC in a leukemia patient, the method comprising administering an effective amount of methyldopa, olanzapine, or both, to the leukemia patient, thereby reducing the number of abnormal PBMC in the leukemia patient.

In some implementations, the number of abnormal PBMC is reduced by 5% to 80% relative to an initial number of abnormal PBMC in the leukemia patient prior to administering the effective amount of methyldopa, olanzapine, or both.

In some implementations, the leukemia patient is afflicted with chronic lymphocytic leukemia.

In some implementations, the method further comprises administering an effective amount of doxorubicin to the leukemia patient together with the administering of the effective amount of methyldopa, olanzapine, or both.

According to a third aspect, the present disclosure relates to a method of reducing a number of abnormal PBMC in a leukemia patient, the method including administering an effective amount of an antibody-drug conjugate including an antibody selected from the group consisting of an anti-$\alpha_2$ adrenoceptor antibody, an anti-β adrenoceptor antibody, an anti-trace amine-associated receptor 1 antibody, an anti-dopamine receptor antibody, and an anti-serotonin receptor antibody; a drug selected from the group consisting of isoproterenol, methyldopa, olanzapine, and a derivative thereof; and a linker that conjugates the antibody and the drug.

In some implementations of the method, the linker comprises an enzymatically cleavable peptide bond, a hydrolysable bond, or both.

In some implementations of the method, the linker comprises the enzymatically cleavable peptide bond and the enzymatically cleavable peptide bond is a dipeptide of valine-citrulline.

In some implementations of the method, the linker comprises the hydrolysable bond and the hydrolysable bond is a carbonate bond.

In some implementations of the method, the linker further comprises a water solubilizing group.

In some implementations of the method, the water solubilizing group is a polyethylene glycol polymer.

In some implementations of the method, the linker further comprises an N-alkyl succinimide.

In some implementations of the method, the administering is an IV infusion.

In some implementations of the method, the PBMC express an $\alpha_2$ adrenoceptor, a $\beta$ adrenoceptor, a trace amine-associated receptor 1, a dopamine receptor, a serotonin receptor, or a combination thereof.

In some implementations, the method further includes a first determining a number of PBMC cells by a cell viability assay based on a luminescence measurement prior to the administering and a second determining of the number of PBMC cells by the cell viability assay based on the luminescence measurement after the administering.

In some implementations of the method, the number of PBMC cells is reduced by 5% to 60% relative to a number of PBMC cells in the leukemia patient prior to administering the antibody-drug conjugate.

In some implementations of the method, the linker includes a self-immolating group (Y), a cleavable group (P), which is a protease sensitive peptide, a water solubilizing group (W), which is selected from the group consisting of a $PEG_4$ to $PEG_8$, and an alkylated-succinimide group that is covalently bound to the antibody.

In some implementations of the method, the self-immolating group is a reacted form of p-amino-benzyl alcohol and is bound to the drug by a carbamate bond or a carbonate bond.

In some implementations of the method, the cleavable group or the self-immolating group is directly bonded to the drug or the derivative of the drug via a carbamate or carbonate bond.

In some implementations of the method, the leukemia is chronic lymphocytic leukemia.

In some implementations, the method further includes administering chlorambucil-prednisone, a drug combination comprising cyclophosphamide, vincristine sulfate, and prednisone, or both.

In some implementations of the method, the antibody-drug conjugate is of the Formula I:

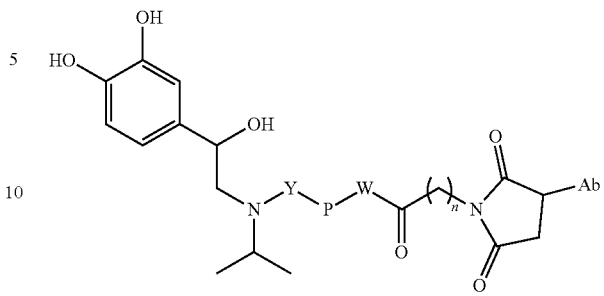

(I)

in which Ab is an antibody selected from the group consisting of an anti-β adrenoceptor antibody and an anti-trace amine-associated receptor 1 antibody, and in which the linker comprises Y, which is a self-immolating group bound to the isoproterenol, P, which is a protease sensitive peptide, W, which is a water solubilizing group, and an N-alkyl-succinimide bound to the water solubilizing group and the antibody (Ab), wherein n is 1 to 8.

In some implementations of the method, the antibody-drug conjugate is of the Formula II:

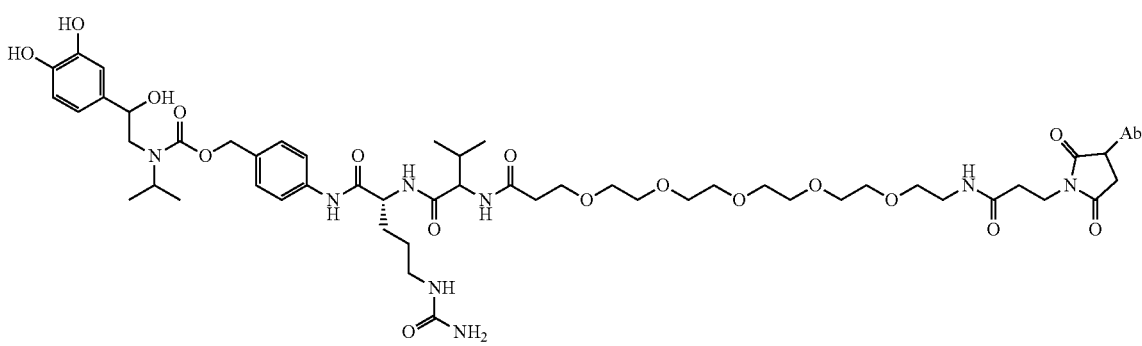

(II)

in which Ab is the antibody.

In some implementations of the method, the antibody-drug conjugate is of the Formula III:

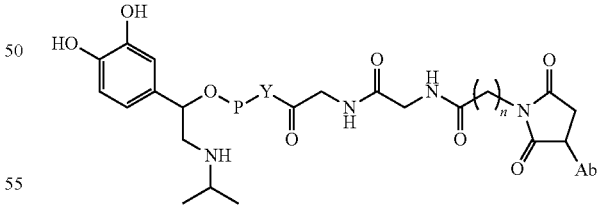

In which Ab is an antibody selected from the group consisting of an anti-β adrenoceptor antibody and an anti-trace amine-associated receptor 1 antibody, and in which the linker comprises P, which is a pH sensitive group, Y, which is a self-immolating group, a glycine-glycine dipeptide, and an N-alkyl-succinimide bound to the glycine-glycine dipeptide and the antibody (Ab), wherein n is 1 to 8.

In some implementations of the method, the antibody-drug conjugate is of the Formula IV:

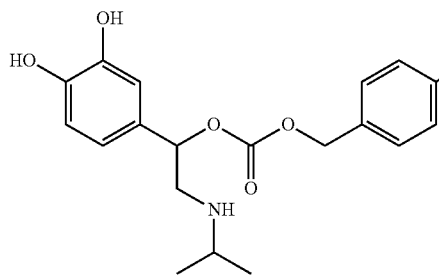
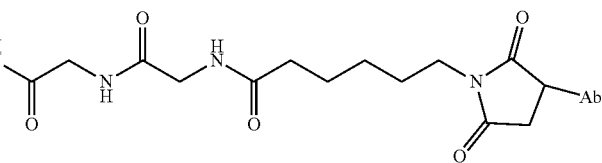

in which Ab is the antibody.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 5A is a chemical scheme for preparing the conjugate of Formula II;

DETAILED DESCRIPTION OF THE EMBODIMENTS

Figure 1A:
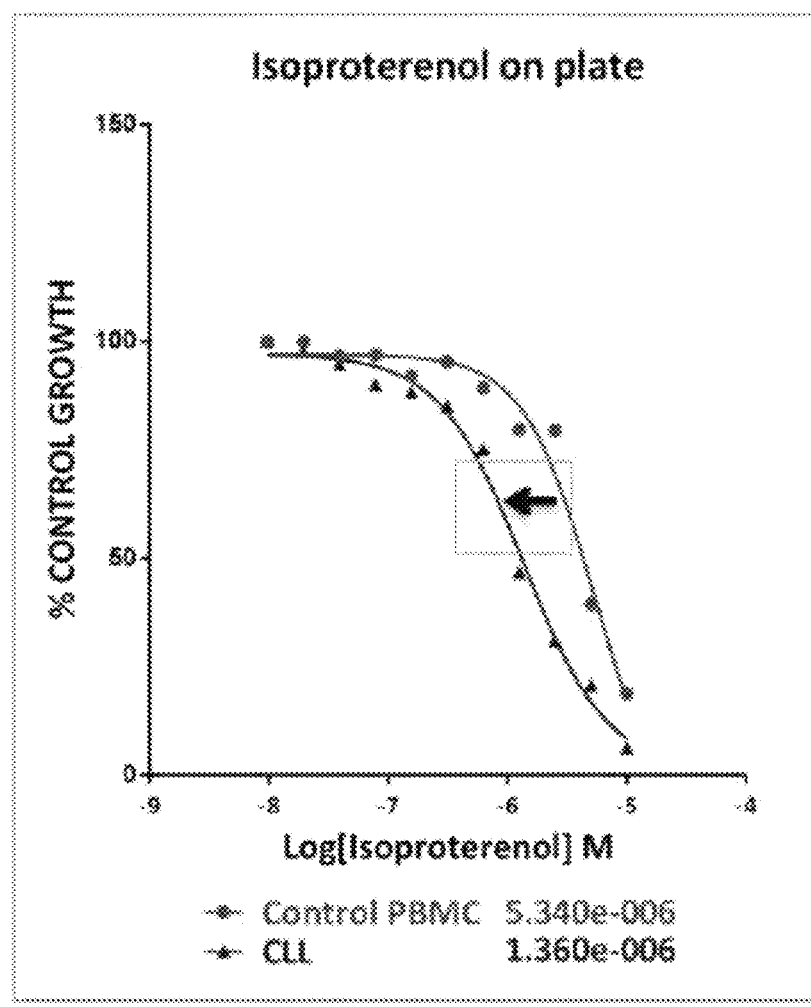
FIG. 1A is a graph depicting the effects of liquid stock isoproterenol on PBMC cells from CLL patients.

Embodiments of the present disclosure will now be described more fully hereinafter with reference to the accompanying drawings, in which some, but not all of the embodiments of the disclosure are shown.

The present disclosure will be better understood with reference to the following definitions.

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

The phrase "pharmaceutically acceptable" as used herein refers to counterions, compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Therefore, the composition refers to the combination of an active ingredient with a pharmaceutically acceptable carrier, inert or active, and/or an excipient, making the composition especially suitable for diagnostic or therapeutic use in vivo or ex vivo. One purpose of a composition is to facilitate administration of the active ingredient to patient.

The terms "active ingredient" and "drug", as used herein, refer to an ingredient in the composition that is biologically active, for example, isoproterenol, methyldopa, olanzapine, doxorubicin, and an antibody-drug conjugate. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

In most implementations of the methods, the composition has one active ingredient and comprises at least 0.5 wt %, at least 5 wt %, at least 10 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, at least 95 wt %, at least 99 wt %, or at least 99.9 wt %, of isoproterenol, methyldopa, olanzapine, or the antibody-drug conjugate. The composition may comprise 0.01-50 µM, 0.01-30 µM, preferably 0.01-10 µM of isoproterenol, methyldopa, olanzapine, or the antibody-drug conjugate.

In some implementations of the methods, the composition has two active ingredients. The composition may comprise at least 0.5 wt %, at least 5 wt %, at least 10 wt %, at least 15 wt %, at least 20 wt %, at least 25 wt %, or at least 30 wt %, and up to 49.5 wt %, up to 45 wt %, up to 40 wt %, or up to 35 wt % of a first active ingredient. The composition may comprise at least 0.5 wt %, at least 5 wt %, at least 10 wt %, at least 15 wt %, at least 20 wt %, at least 25 wt %, or at least 30 wt %, and up to 49.5 wt %, up to 45 wt %, up to 40 wt %, or up to 35 wt % of a second active ingredient. In some implementations of the methods, the first active ingredient is isoproterenol, methyldopa, olanzapine, or the antibody-drug conjugate, and the second active ingredient is doxorubicin, a salt thereof (e.g. a hydrochloride salt), or a prodrug thereof. In some implementations of the methods, the second active ingredient is cytarabine, daunorubicin, idarubicin, ivermectin, apomorphine hydrochloride hemihydrate, auranofin, lapatinib ditosylate, disulfiram, digoxin, mefloquine, silver sulfadiazine, adefovir dipivoxil, sertraline, cyclosporine A, pimozide, loperamide, flecainide acetate, dobutamine, or any one of the drugs listed in Table 1. In some implementations, the composition comprises a drug combination (e.g., chlorambucil-prednisone; a combination comprising cyclophosphamide, vincristine sulfate, and prednisone; or both) in addition to the first active ingredient.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

The present disclosure is further intended to include all isotopes of atoms occurring in the present compounds. Isotopes include those atoms having the same atomic number but different mass numbers. By way of general example, and without limitation, isotopes of hydrogen include deuterium and tritium. Isotopes of carbon include $^{13}$C and $^{14}$C. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

The present disclosure relates to methods of reducing the number of abnormal peripheral blood mononuclear cells (PBMC) in a leukemia patient, who may be afflicted with acute lymphoblastic leukemia (ALL), acute myeloid leukemia (AML), chronic lymphocytic leukemia (CLL), or chronic myeloid leukemia (CML). In some implementations of the method, the leukemia patient is afflicted with chronic lymphocytic leukemia or chronic myelogenous leukemia. As used herein, a peripheral blood mononuclear cell is any peripheral blood cell having a round nucleus. These cells include lymphocytes (T cells, B cells, NK cells) and monocytes. Abnormal PBMC may be defined as cells that have genetic markers for leukemia. For example, abnormal PBMC may comprise chromosomal deletions of 11q-, 13-q, 17p- and trisomy 12, which are indicative of CLL in patients. In some implementations of the method, the abnormal PBMC express an $\alpha_2$ adrenoceptor, a $\beta$ adrenoceptor, a trace amine-associated receptor 1 (TAAR1), a dopamine receptor (e.g. D2, D3, and D4), a serotonin receptor (e.g., a 5-HT receptor) or a combination thereof. The abnormal PBMC may overexpress the aforementioned receptors. As used herein, "overexpress" refers to having an excess of the receptors on the surface of a cell. Each of the aforementioned receptors may be independently overexpressed by at least 10%, at least 15%, or at least 30%, and up to 500%, up to 400%, up to 300%, or up to 200%, relative to the number of receptors on the surface of a normal PBMC cell from a healthy person i.e. not afflicted by ALL, AML, CLL, or CML.

The term "effective amount" refers to an amount of a drug effective for treating a disease or disorder in a mammal. In the case of cancer, the effective amount of the drug may: (i) reduce the number of abnormal PBMC by at least 5%, at least 10%, at least 20%, at least 30%, or at least 40%, and up to 100%, up to 99%, up to 95%, up to 90%, up to 80%, or up to 60%, relative to an initial number of abnormal PBMC cells; (ii) reduce a tumor size by at least 5%, at least 10%, at least 20%, at least 30%, or at least 40%, and up to 99%, up to 95%, or up to 90%; (iii) inhibit, retard, slow to some extent and preferably stop PBMC cell proliferation; (iv) inhibit (i.e., slow to some extent and preferably stop) tumor metastasis; (v) inhibit tumor growth; and/or (vi) relieve to some extent one or more of the symptoms associated with the leukemia. To the extent the drug may prevent growth and/or kill existing cancerous PBMC cells, it may be cytostatic and/or cytotoxic. In animal models, efficacy may be assessed by counting of PBMC in patient bone marrow during a course following administration of the drug, and by determining partial and complete remission of leukemia. For leukemia therapy, efficacy can, for example, be measured by assessing the time to disease progression (TTP) and/or determining the response rate (RR). In some implementations, the drug may be administered, for example, intravenously, to a patient at 50 ng/mL to 500 ng/mL, 75 ng/mL to 400 ng/mL, 100 ng/mL to 300 ng/mL, or 200 ng/mL to 250 ng/mL. In some implementations, the drug may be administered to a patient at 1-100 mg/kg of the patient's body weight, or at least 5 mg/kg, at least 10 mg/kg, at least 20 mg/kg, or at least 30 mg/kg, and up to 100 mg/kg, up to 90 mg/kg, up to 80 mg/kg, up to 70 mg/kg, or up to 60 mg/kg. In some implementations, two drugs may be administered to the patient. The first drug may be administered at 1-100 mg/kg body weight, or at least 5 mg/kg, at least mg/kg, at least 20 mg/kg, or at least 30 mg/kg, and up to 100 mg/kg, up to 90 mg/kg, up to 80 mg/kg, up to 70 mg/kg, or up to 60 mg/kg. The second drug may be administered at 1-100 mg/kg body weight, or at least 5 mg/kg, at least 10 mg/kg, at least 20 mg/kg, or at least 30 mg/kg, and up to 100 mg/kg, up to 90 mg/kg, up to 80 mg/kg, up to 70 mg/kg, or up to 60 mg/kg, so that a total amount of the first and second drugs does not exceed 200 mg/kg. In some implementations, the drug is administered at a dose required to maintain 90% occupancy of at least one of an $\alpha_2$ adrenoceptor, a $\beta$ adrenoceptor, a trace amine-associated receptor 1, a dopamine receptor, a serotonin receptor on abnormal PBMC cells.

The terms "administer", "administering", "administration", and the like, as used herein, refer to the methods that may be used to enable delivery of the active ingredient and/or the composition to the desired site of biological action. In some implementations, the drug may be administered to a leukemia patient who is simultaneously undergoing chemotherapeutic treatment, spinal based drugs, or radiation treatment. In some implementations, the drug is administered after a bone marrow transplant procedure.

Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. In some implementations of the method, the administering is an IV infusion. Those of ordinary skill in the art are familiar with administration techniques that can be employed with the compounds and methods described herein.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavoring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration can also involve the use of transdermal administration such as transdermal patches or iontophoresis devices. Formulation of drugs is discussed in, for example, Hoover, John E., Remington's Pharmaceutical Sciences, Mack Publishing Co., Easton, Pa., 1975. Another example of includes Liberman, H. A. and Lachman, L., Eds., Pharmaceutical Dosage Forms, Marcel Decker, New York, N.Y., 1980, which is incorporated herein by reference in its entirety).

The schedule of administration may comprise administration once or twice a week, on a cycle selected from the group consisting of: (i) weekly; (ii) every other week; (iii) one week of therapy followed by two, three or four weeks off; (iv) two weeks of therapy followed by one, two, three or four weeks off; (v) three weeks of therapy followed by one, two, three, four or five week off; (vi) four weeks of therapy followed by one, two, three, four or five week off; (vii) five weeks of therapy followed by one, two, three, four or five week off; and (viii) monthly. The cycle may be repeated 2, 4, 6, 8, 10, or 12 times or more. In some implementations of the methods, the composition is administered at various dosages (e.g. a first dose with an effective amount of 50 mg/kg and a second dose with an effective amount of 10 mg/kg).

Alternatively, the drug may be administered as one dosage every 2 or 3 weeks, repeated for a total of at least 3 dosages. Or, twice per week for 4-6 weeks. The dosage may be administered once every other week or even less frequently, so the patient can recover from any drug-related toxicities. Alternatively, the dosage schedule may be decreased, namely every 2 or 3 weeks for 2-3 months. The dosing schedule can optionally be repeated at other intervals.

In some implementations, the patient has a high disease burden and is sensitive to treatment with the drugs described by the present disclosure. High disease burden may, be indicated by white blood cell counts which exceed 15,000 cells/μL, exceed 20,000 cells/μL, or 25,000 cells/μL in a total blood cell count procedure. In some implementations of the method, a loading dose for such patient is 2.0 mg/kg body weight and is administered on days one and eight of a three week cycle. The loading dose can be administered in a single three week cycle or two three or four loading doses can be administered before a maintenance dose is started. The 2 mg/kg maintenance dose is administered on day one of a three week cycle for multiple three week cycles. In some implementations, maintenance doses are given for between one and ten three week cycles. In some implementations, maintenance doses are given for between ten and twenty three week cycles.

Isoproterenol is a medication used for the treatment of bradycardia, heart block, and asthma. In humans, isoproterenol is a non-selective β adrenoceptor agonist and trace amine-associated receptor 1 (TAAR1) agonist and is structurally similar to epinephrine. Isoproterenol is dosed to adults for respiratory and cardiac disorders at 0.01 mg to 0.06 mg, or 0.05 mg to 0.055 mg as an IV bolus or an IV infusion and for shock doses 0.5 to 5 μg/min, 0.75 to 4 μg/min, 1 to 3 μg/min, or 2 to 2.5 μg/min as an IV infusion.

The present disclosure describes isoproterenol's effectiveness in killing PBMC from chronic lymphoid leukemia patients. In one embodiment, the cells may be incubated in vitro with isoproterenol for at least 1 hour, at least 5 hours, or at least 24 hours, and up to 72 hours, up to 56 hours, or up to 48 hours. A concentration of isoproterenol may be at least 0.001 μM, at least 0.01 μM, at least 0.1 μM, or at least 1 μM, and up to 1,000 μM, up to 100 μM, or up to 10 μM. After the incubation, the cell viability may be measured with the assays described hereinafter. The EC50 of isoproterenol in abnormal PBMC from chronic lymphoid leukemia patients may be in a range of 1-20 μM, 1-10 μM, or 1-4 μM, which may be at least 3 times higher, at least 5 times higher, or at least 6 times higher, and up to 10 times higher, up to 8 times higher, or up to 7 times higher than the EC50 of isoproterenol in PBMC from a healthy person. As used herein, the term "EC50" refers to the concentration of a drug that reduces the viability of the PBMC by 50%. The EC50 may be measured by a CellTiter-Glo® assay, CellTiter-Blue™ assay, CellTiter 96® assay, CytoTox-One™ membrane integrity assay, Apo-One® homogeneous caspase-3/7 assay, or a Caspase-Glo™ 3/7 assay.

The first aspect of the disclosure relates to a method of reducing a number of abnormal PBMC in a chronic myelogenous leukemia patient. The method comprises administering an effective amount of isoproterenol to the chronic myelogenous leukemia patient. In one embodiment, the cells may be incubated in vitro with isoproterenol for at least 1 hour, at least 5 hours, or at least 24 hours, and up to 72 hours, up to 56 hours, or up to 48 hours. A concentration of isoproterenol may be at least 0.001 μM, at least 0.01 μM, at least 0.1 μM, or at least 1 μM, and up to 1,000 μM, up to 100 μM, or up to 10 μM. After the incubation, the cell viability may be measured with the assays described herein. The EC50 of isoproterenol in abnormal PBMC from the chronic myelogenous leukemia patient may be in a range of 1-20 μM, 1-10 μM, or 2-5 μM, which may be at least 3 times higher, at least 5 times higher, or at least 6 times higher, and up to 10 times higher, up to 8 times higher, or up to 7 times higher than the EC50 of isoproterenol in PBMC from a healthy person.

Methyldopa, sold under the brand name Aldomet among others, is a centrally acting antihypertensive agent. Without wishing to be bound by theory, methyldopa may activate central $α_2$ adrenergic receptors. Being a selective agonist for $α_2$ adrenergic receptors, methyldopa is used as a sympatholytic or antihypertensive. Commonly methyldopa is dosed to patients of hypertension at 250 mg orally 2-3 times a day or 250 to 500 mg, 275 to 450 mg, or 300 to 400 mg IV over 30 to 60 minutes, or 40 to 50 minutes every 6 hours, up to a maximum of 3 g/day. Previously, methyldopa was not reported to exhibit PBMC killing activity.

Olanzapine, branded as Zyprexa, is an atypical antipsychotic used for the treatment of schizophrenia and bipolar disorder. Olanzapine is structurally similar to clozapine and quetiapine. Olanzapine is a dopamine antagonist and is classified as a thienobenzodiazepine. Olanzapine exerts its effect through binding and antagonizing human dopamine D2, D3 and D4 and 5-HT receptor. For treating mental health conditions, olanzapine is dosed to patients at 5 to 20 mg, or 10 to 15 mg orally at least once a day, at least twice a day or at least 4 times a day. Previously, olanzapine was not reported to exhibit PBMC killing activity.

Therefore, the second aspect of the disclosure relates to a method of reducing a number of abnormal PBMC in a leukemia patient. The method comprises administering an effective amount of methyldopa, olanzapine, or both to the leukemia patient. The leukemia patient may be afflicted with chronic lymphocytic leukemia.

Figure 3A:
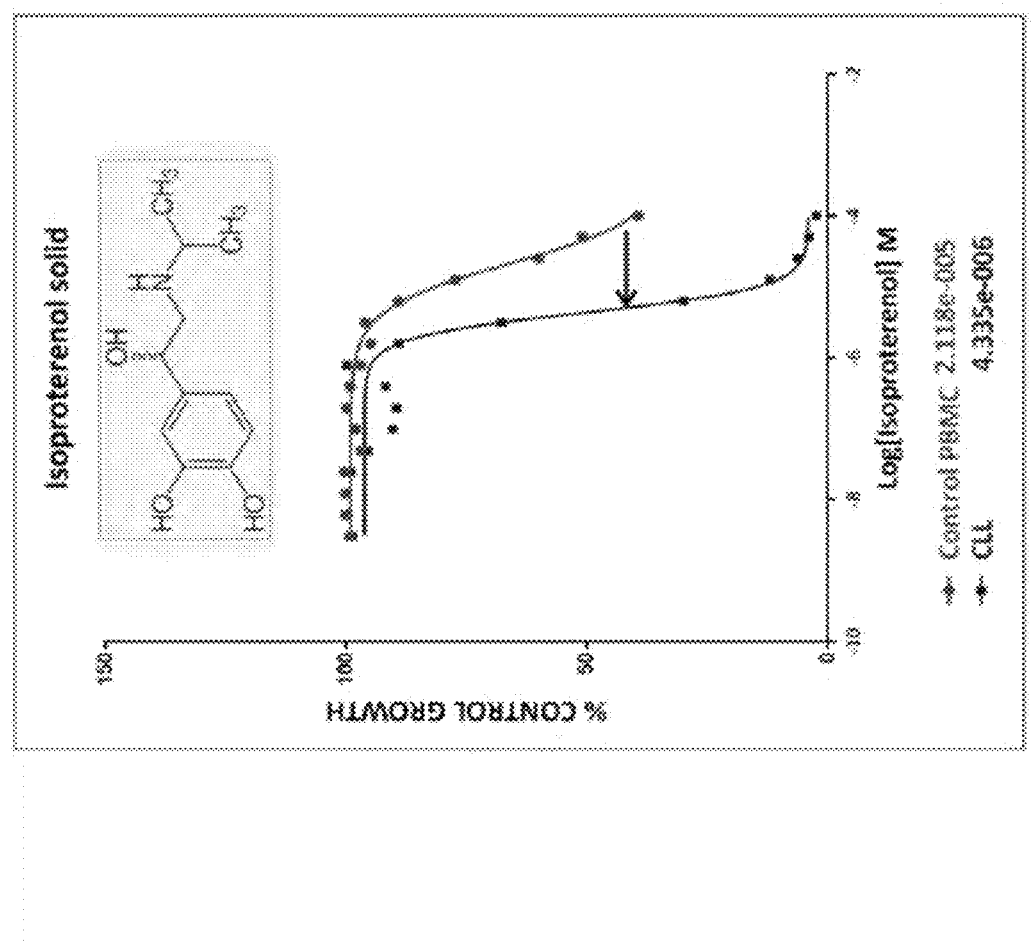
FIG. 3A is a graph depicting the EC50 of isoproterenol in PBMC cells from CLL patients and healthy individuals.
Figure 3B:
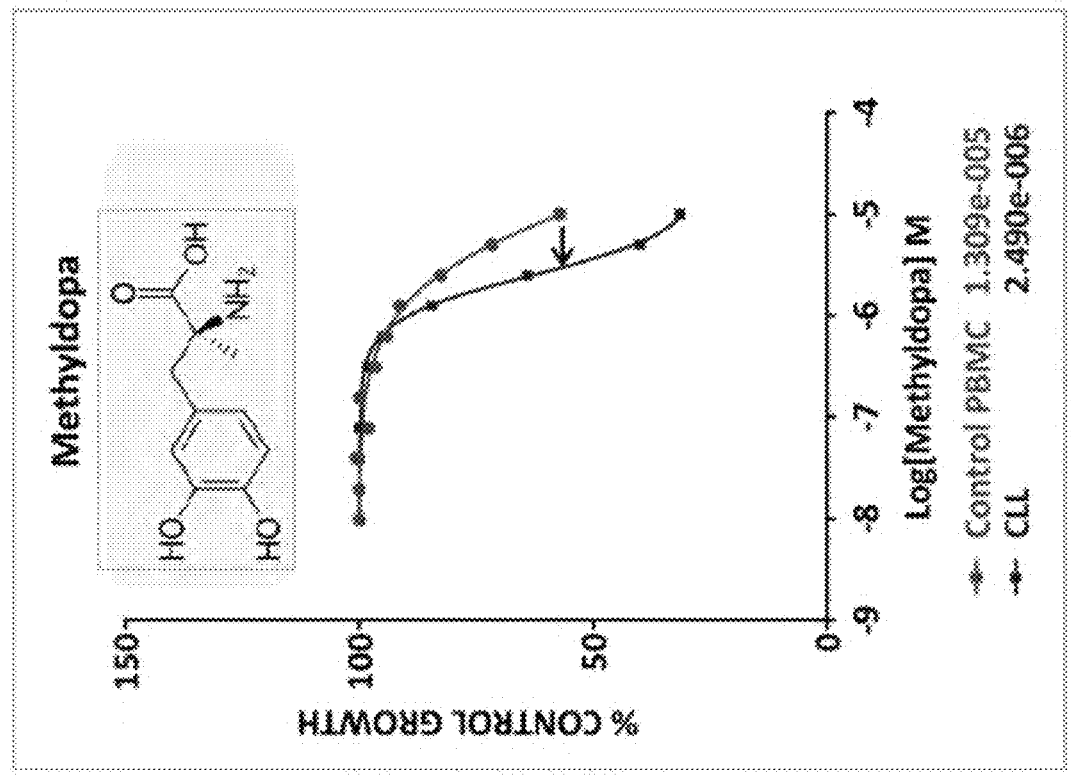
FIG. 3B is a graph depicting the EC50 of methyldopa in PBMC cells from CLL patients and healthy individuals.

FIG. 3A and FIG. 3B depict graphs indicating the effectiveness of methyldopa against PBMC derived from patient having chronic lymphoid leukemia.

In one embodiment, the cells may be incubated in vitro with methyldopa, olanzapine, or both for at least 1 hour, at least 5 hours, or at least 24 hours, and up to 72 hours, up to 56 hours, or up to 48 hours. A concentration of methyldopa, olanzapine, or both may be at least 0.001 μM, at least 0.01 μM, at least 0.1 μM, or at least 1 μM, and up to 1,000 μM, up to 100 μM, or up to 10 μM. For example, when both methyldopa and olanzapine are present, a total concentration of both drugs is at least 0.001 M, at least 0.01 μM, at least 0.1 μM, or at least 1 μM, and up to 1,000 μM, up to 100 μM, or up to 10 μM. A concentration ratio of methyldopa to olanzapine may be in a range of 1:99 to 99:1, 10:90 to 90:10, 20:80 to 80:20, 30:70 to 70:30, 40:60 to 60:40, or about 50:50. After the incubation, the cell viability may be measured with the assays described herein. In one embodiment where only methyldopa is present (i.e., olanzapine is absent), the EC50 of methyldopa in abnormal PBMC from the leukemia patient may be in a range of 1-20 μM, 1-10 μM, or 2-5 μM, which may be at least 3 times higher, at least 5 times higher, or at least 6 times higher, and up to 10 times higher, up to 8 times higher, or up to 7 times higher than the EC50 of methyldopa in PBMC from a healthy person.

Methyldopa is structurally related to isoprenaline. Both the drug has dihydroxy phenol (catechol) as core and both the hydroxyl groups are positioned at 3, and 4 of the benzene ring in methyldopa and isoprenaline.

Similarity in the position of hydroxyl group suggests that both the drugs may be mechanistically acting to induce cell death in the leukemia cells in a similar way.

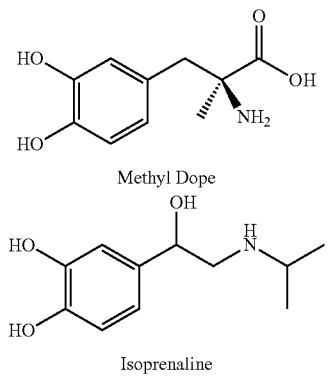

Methyl Dope

Isoprenaline

Both the thugs have amine functionality, secondary amine in isoprenaline and primary amine in case of methyldopa. Both adrenergic and dopaininergic pathways have some link to leukemia but have not been developed as target to treat leukemia.

FIG. 4A-FIG. 4D depict graphs indicating the effectiveness of olanzapine against PBMC derived from patient having chronic lymphoid leukemia.

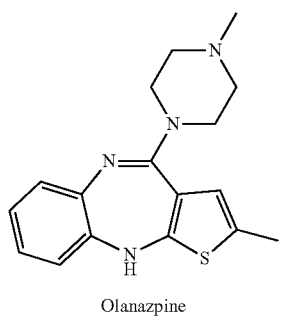

Olanazpine

In one embodiment where olanzapine is present, the EC50 of olanzapine in abnormal PBMC from the leukemia patient may be in a range of 1-300 μM, 10-260 μM, or 10-50 μM, which may be at least 2 times higher, at least 4 times higher, or at least 6 times higher, and up to 10 times higher, up to 8 times higher, or up to 7 times higher than the EC50 of olanzapine in PBMC from a healthy person.

The third aspect of the disclosure relates to a method for reducing a number of abnormal PBMC in a leukemia patient. The method comprises administering an effective amount of an antibody-drug conjugate to the leukemia patient.

The antibody-drug conjugate (ADC) of the present disclosure includes an antibody which may be an anti-$\alpha_2$ adrenoceptor antibody, an anti-β adrenoceptor antibody, an anti-trace amine-associated receptor 1 (anti-TAAR1) antibody, an anti-dopamine receptor antibody, or an anti-serotonin receptor antibody. The ADC includes a drug selected from the group consisting of isoproterenol, methyldopa, olanzapine, and a derivative thereof; and a linker that conjugates the antibody and the drug. Kamp et al, Lamkin et al, and Wasik et al. describe andrenergic receptor and TAAR1 receptor signaling pathways implicated in leukemia. See Kamp T1, Liebl B, Haen E, Emmerich B, Hallek M., "Defects of beta 2-adrenergic signal transduction in chronic lymphocytic leukaemia: relationship to disease progression," Eur J Clin Invest. 1997 Feb., 27(2):121-7; Lamkin D M1, Sloan E K, Patel A J, Chiang B S, Pimentel M A, Ma J C, Arevalo J M, Morizono K, Cole S W. "Chronic stress enhances progression of acute lymphoblastic leukaemia via β-adrenergic signaling," Brain Behav Immun. 2012 May, 26(4):635-41, Epub 2012, January 25; Wasik A M1, Millan M J, Scanlan T, Barnes N M, Gordon J. "TAAR1 has been linked to leukaemia," Leuk Res. 2012 February; 36(2):245-9, Epub 2011, October 27, each incorporated herein by reference in their entirety. A derivative may include isoproterenol having a protected amine or hydroxyl, methyldopa having a protected amine or carboxylic acid, or an olanzapine having the piperazine substituted by an ethyl group, butyl group, or hydroxyethyl group (e.g. 2-Methyl-4-[4-ethyl-1-piperazinyl)-10H-thieno[2,3-b][1,5]benzodiazepine).

The leukemia patient's response to the treatment may be monitored by measuring the complete blood count, which includes red blood cell count, white blood cell count, platelet count, a concentration of hemoglobin, and a concentration of hematocrit. The complete blood count or at least one of its components (e.g., white blood cell count) may return to normal levels within 4 weeks, 6 weeks, or 10 weeks of the start of the treatment. A normal red blood cell count is in a range of 4.32-5.72 trillion cells/L (for males) or 3.90-5.03 trillion cells/L (for females). A normal white blood cell count is in a range of 3.5-10.5 billion cells/L. A normal platelet count is in a range of 150-450 billion/L. A concentration of hemoglobin is in a range of 135-175 grams/L (for males) or 120-155 grams/L (for females). A normal level of hematocrit is in a range of 38.8-50.0% (for males) or 34.9-44.5% (for females). In some embodiments in which the patient is afflicted with chronic myeloid leukemia, the hemoglobin concentration, the white blood cell count, and the platelet count return to normal levels after the aforementioned duration. In some embodiments in which the patient is afflicted with chronic lymphocytic leukemia, the white blood cell count returns to the normal level after the aforementioned duration. Further, the hemoglobin concentration or the platelet count may also return to normal levels if autoimmune hemolytic anemia or immune thrombocytopenia, respectively, is present at the time of diagnosis.

The leukemia patient's response to the treatment may also be monitored by observing the disappearance/reduction in occurrences of abnormal cytogenetic markers detected at the time of diagnosis. For example, in chronic myeloid leukemia patients, the abnormal cytogenetic marker is a Philadelphia chromosome (t9:22 translocation). The disappearance or the reduction may be observed 1-12 months, 2-8 months, or 3-6 months from the start of the treatment. Complete disappearance of the abnormal cytogenetic marker is termed complete cytogenetic response (CcyR) and reduction of the abnormal cytogenetic marker is termed major cytogenetic response (McyR). The reduction in occurrences of the abnormal cytogenetic marker may be at least 5%, at least 10%, at least 20%, at least 30%, at least 40%, at least 50%, at least 60%, at least 70%, at least 80%, at least 90%, at least 95%, or at least 98%, and less than 100% of the original number of occurrences (i.e., before the start of the treatment). Conventional cytogenetic analysis or FISH analysis may be useful for observing the disappearance/reduction of the abnormal cytogenetic markers.

The leukemia patient's response to the treatment may also be monitored by observing the disappearance/reduction in occurrences of BCR/ABL mutational copies detected at the time of diagnosis. Complete disappearance of the BCR/ABL mutational copies is termed complete molecular response (CMR) and reduction of the BCR/ABL mutational copies is termed major molecular response (MMR). The reduction in occurrences of the BCR/ABL mutational copies may be at least 5%, at least 10%, at least 20%, at least 30%, at least 40%, at least 50%, at least 60%, at least 70%, at least 80%, at least 90%, at least 95%, or at least 98%, and less than 100% of the original number of occurrences (i.e., before the start of the treatment). A polymerase chain reaction (PCR) may be useful for observing the disappearance/reduction in occurrences of BCR/ABL mutational copies.

The leukemia patient's response to the treatment may also be monitored by observing the disappearance of any constitutional symptoms (e.g., fatigue, weakness, itching, fever, night sweats, and weight loss) where associated with disease at time of presentation.

The leukemia patient's response to the treatment may also be monitored by observing the reduction in the size of the enlarged lymph nodes compared to their size at the time of diagnosis. For example, the size of the enlarged lymph nodes may reduce by at least 5%, at least 10%, at least 20%, at least 30%, or at least 40%, and up to 99%, up to 95%, or up to 90%.

The present disclosure relates to a method of identifying drugs, such as isoproterenol, methyldopa, and olanzapine, by employing proliferated primary cells from patients diagnosed with a targeted disorder. Primary cells may be employed in a cell population or single cell analysis of a drug's effects on a cell. The primary cells may have been collected 1 day to 10 days, 2 days to 8 days, or 3 days to 6 days prior to testing for a drugs effect on the cells. Further the cells employed may not be employed for more than 60 replications, more than 50 replications, or more than 30 replications. Replications cycles may also be referred to as passages or media exchanges to maintain the cell growth. The cells are not frozen and were not frozen at any time in the growth of the cells. For example, cells may be employed in a cell death assay on a multi-well plate with a population of primary cells proliferated from a patient diagnosed with leukemia (CLL, ALL, CIVIL) are conducted on unfrozen cells.

In some implementations of the method, the term "antibody" also encompasses genetically engineered intact antibodies or fragments such as, for example, chimeric antibodies, humanized antibodies, "Fv" fragments consisting of the variable regions of the heavy and light chains, polypeptides consisting of the light chain variable region, recombinant single chain antibodies in which light and heavy variable regions are connected by a peptide linker ("scFv proteins"), minimal recognition units consisting of the amino acid residues that mimic the hypervariable region, and the like, as well as synthetic antigen-binding peptides and polypeptides. A "chimeric antibody" is a recombinant protein that contains the variable domains and complementary determining regions derived from a rodent antibody, while the remainder of the antibody molecule is derived from a human antibody. "Humanized antibodies" are recombinant proteins in which murine complementarity determining regions of a monoclonal antibody have been transferred from heavy and light variable chains of the murine immunoglobulin into a human variable domain. Construction of humanized antibodies for therapeutic use in humans that are derived from murine antibodies, such as those that bind to or neutralize a human protein, is within the skill of one in the art. The antibody may be monoclonal or polyclonal. The antibody may be sourced from a rabbit, a mouse, a chicken, or a horse. The antibody includes an antibody fragment such as an Fc fragment. The terms "Fc fragment," "Fc region," or "Fc domain," as used herein, are synonymous and refer to the portion of an antibody that is responsible for binding to antibody receptors on cells and the C1q component of complement. Fc stands for "fragment crystalline," the fragment of an antibody that will readily form a protein crystal. Distinct protein fragments, which were originally described by proteolytic digestion, can define the overall general structure of an immunoglobulin protein. As originally defined in the literature, the Fc fragment includes the disulfide-linked heavy chain hinge regions, $CH_2$, and $CH_3$ domains. However, more recently the term has been applied to a single chain consisting of $CH_3$, $CH_2$, and at least a portion of the hinge sufficient to form a disulfide-linked dimer with a second such chain. For a review of immunoglobulin structure and function, see Putnam, The Plasma Proteins, Vol. V (Academic Press, Inc., 1987), pp. 49-140; and Padlan, Mol. Immunol. 31:169-217, 1994. As used herein, the term Fc includes variants of naturally occurring sequences.

A linker is a bifunctional compound which can be used to link a drug and an antibody to form an antibody-drug conjugate. Such conjugates are useful, for example, in the formation of immunoconjugates directed against tumor associated antigens. Such conjugates allow the selective delivery of cytotoxic drugs to tumor cells. In some implementations of the method the linker comprises an enzymatically cleavable peptide bond, a hydrolysable bond, or both.

The enzymatically cleavable peptide bond may be sensitive to proteases in the blood, at the site of a PBMC cell surface, intracellular to the PBMC cell, or in an endosome, including a lysosome of a PBMC cell. Hereafter, the enzymatically cleavable peptide may be referred to as a protease sensitive peptide. An enzymatic cleavage reaction on the ADC will remove the linker moiety or initiate a cascade reaction to remove the linker moiety from the drug conjugate and effect release of the antitumor agent in pharmacologically active form selectively at the PBMC cell site. In some implementations of the method, the enzymatically cleavable peptide bond is a dipeptide of valine-citrulline, phenylalanine-lysine, valine-lysine, phenylalanine-phenylalanine-lysine, D-phenylalanine-lysine, alanine-lysine, phenylalanine-citrulline, leucine-citrulline, isoleucine-citrulline, tryptophan-citrulline, phenylalanine-alanine. The hydrolysable bond may be a pH sensitive bond. In some implementations of the method, the hydrolysable bond is a carbonate bond or a phosphoramidate ester bond.

In some implementations of the method, the ADC may include an intermediate self-immolative spacer moiety which spaces and covalently links together the drug moiety and the protein peptide moiety directly or indirectly as a part of a larger linker. A self-immolative spacer may be defined as a bifunctional chemical moiety which is capable of covalently linking together two spaced chemical moieties into a normally stable tripartate molecule. Releasing one of said spaced chemical moieties from the tripartate molecule by means of enzymatic cleavage. Following said enzymatic cleavage, the tripartite molecule spontaneously cleaves from the remainder of the molecule to release the other of said spaced chemical moieties. In accordance with the present invention, the self-immolative spacer is covalently linked at one of its ends to the enzymatically cleavable peptide and covalently linked at its other end to the chemical reactive site of the drug moiety whose derivatization inhibits pharmacological activity, so as to space and covalently link together the protein peptide moiety and the drug moiety into a tripartate molecule. The tripartite molecule is stable and pharmacologically inactive in the absence of the target enzyme, but is enzymatically cleavable by such target enzyme at the bond covalently linking the spacer moiety and the protein peptide moiety to effect release of the protein peptide moiety from the tripartate molecule. Such enzymatic cleavage, in turn, will activate the self-immolating character of the spacer moiety and initiate spontaneous cleavage of the bond covalently linking the spacer moiety to the drug moiety to effect release of the drug in pharmacologically active form. In some implementations of the method, the self-immolating group is a reacted form of p-amino-benzyl alcohol and is bound to the drug by a carbamate bond or a carbonate bond. In some implementations of the method, the cleavable group or the self-immolating group is directly bonded to the drug or the derivative of the drug via a carbamate or carbonate bond.

In some implementations of the method, the linker further comprises a water solubilizing group. The ADC is a large macromolecular structure, solubility may become challenging and thus the solubilizing group may provide for increased circulation in the blood of a patient in need of treatment. The ADC may be 100 kDa to 300 kDa, 150 kDa to 250 kDa, or 175 kDa to 200 kDa. In some implementations of the method, the water solubilizing group is a polyethylene glycol (PEG) polymer. The PEG polymer may be a number average molecular weight range of 800 Da to 3 kDa, 1.5 kDa to 2.5 kDa, or 1.75 kDa to 2.25 kDa. PEG polymers with low molecular weight may enhance the solubility of the ADC.

In some implementations of the method, the linker further comprises a reacted form of a maleimide. Exemplary maleimides, which can be used to form the completed linker portion and subsequently conjugated to an antibody to form the antibody-drug conjugates, may include, but are not limited to N-(2-hydroxyethyl)maleimide, 4-maleimidobutyric acid, 6-maleimidohexanoic acid, each in reacted form. In the presently disclosed ADC a maleimide may be linked to polyethyleneglycol oligomer or polymer. The maleimide group linked to polyethylene glycol polymer may be used as flexible linker to bind the antibody, as described herein, via a cysteine residue on the backbone of the antibody. The cysteine residue may be naturally occurring or engineered into the antibody. In some implementations attachment of the linker to the antibody may be accomplished through surface lysines, reductive-coupling to oxidized carbohydrates, or through cysteine residues liberated by reducing interchain disulfide linkages. A variety of antibody-drug conjugate linkage systems are known in the art, including hydrazone-, disulfide- and peptide-based linkages.

In some implementations, the ADC has a Drug to Antibody Ratio (DAR) of 1 to 5, or 2 to 4.

The structure of the presently described ADC is a drug linked by a reactive amine or hydroxyl. Each of the drugs described herein, or a derivative of the drugs described herein, are each capable of bonding to a linker as described herein by an amine or hydroxyl. Further the bond between the drug and the linker may be to a self-immolating group that is part of the linker, or a cleavable linker as described herein. The cleavable linker or the self-immolating group may then be linked to the water solubilizing group, which in turn may be linked to a maleimide group or alkyl group substituted by a maleimide. The maleimide is linked to the antibody via cysteine, as described herein.

Examples of the structure of the above described schematic of the ADC are as follows.

In some implementations of the method, the linker includes a self-immolating group (Y), a cleavable group (P), which is a protease sensitive peptide, a water solubilizing group (W), which is selected from the group consisting of a PEG$_4$ to PEG$_8$, and a succinimide group that is covalently bound to the antibody.

In some implementations of the method, the antibody-drug conjugate includes an isoproterenol payload ("the drug") and is of the Formula I:

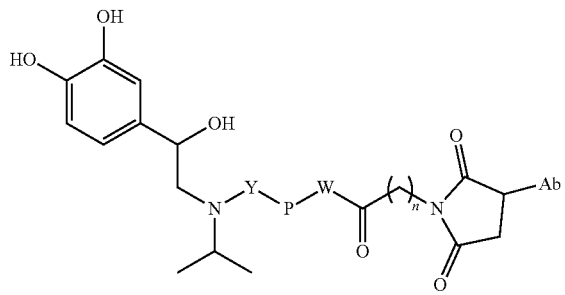

(I)

in which Ab is an antibody selected from the group consisting of an anti-β adrenoceptor antibody and an anti-trace amine-associated receptor 1 antibody, and in which the linker comprises Y, which is a self-immolating group bound to the isoproterenol, P, which is a protease sensitive peptide, W, which is a water solubilizing group, and an N-alkyl-succinimide bound to the water solubilizing group and the antibody (Ab), wherein n is 1 to 8.

In some implementations of the method, the antibody-drug conjugate includes an isoproterenol payload and is of the Formula II:

alcohol, a protease cleaving di-peptide (Val-Cit), a water solubilizing group (PEG), and a cysteine attachment point) can be synthesized as in art. Protected Isoproterenol (A) can be made as described by Mitchell A. Avery, Michael S. Verlander, Murray Goodman, in "Synthesis of 6-aminoisoproterenol," Journal of Organic Chemistry and coupled in presence of a base to the linker to afford intermediate C. See Mitchell A. Avery, Michael S. Verlander, Murray Goodman, in "Synthesis of 6-aminoisoproterenol," Journal of Organic Chemistry, Jul. 1, 1980, pp. 2750-2753, incorporated herein by reference in its entirety. Intermediate C may be synthetically deprotected as described in the art and finally coupled with the antibody. In some implementations the antibody of Formula II will be the anti-beta adrenoceptor antibody and anti-trace amine associated receptor 1 antibody. The antibodies may be commercially available or produced in-house with phage display technology.

In some implementations of the method, the antibody-drug conjugate includes an isoproterenol payload and is of the Formula III:

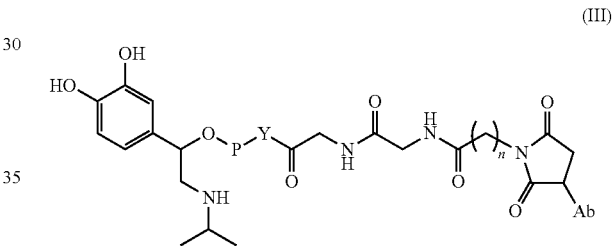

(III)

in which Ab is an antibody selected from the group consisting of an anti-β adrenoceptor antibody or an anti-trace amine-associated receptor 1 antibody, and in which the linker comprises P, which is a pH sensitive group, Y, which is a self-immolating group, a glycine-glycine dipeptide, and an N-alkyl-succinimide bound to the glycine-glycine dipeptide and the antibody (Ab), wherein n is 1 to 8.

(II)

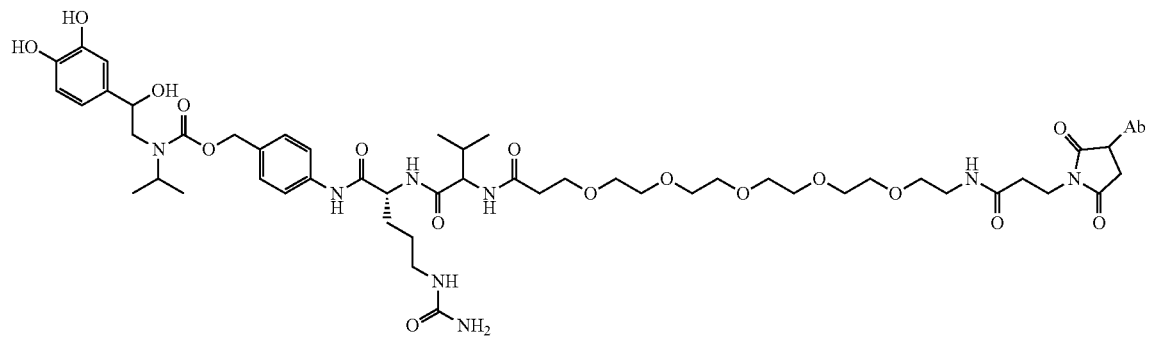

wherein Ab is the antibody.

FIG. 5A depicts Scheme 1 which describes an exemplary synthesis of Formula II. As shown in scheme 1 (FIG. 5A), a linker (B) having a self-immolating group (p-amino benzyl Some implementations of the method described herein, the ADC may exclude the water solubilizing group. For example, in some implementations of the method, the antibody-drug conjugate is of the Formula IV:

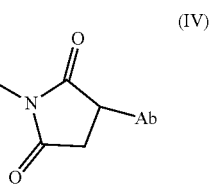
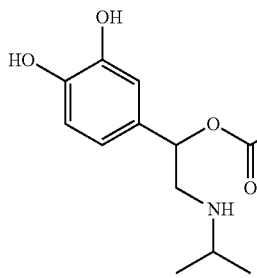

(IV)

in which Ab is the antibody.

Figure 5B:
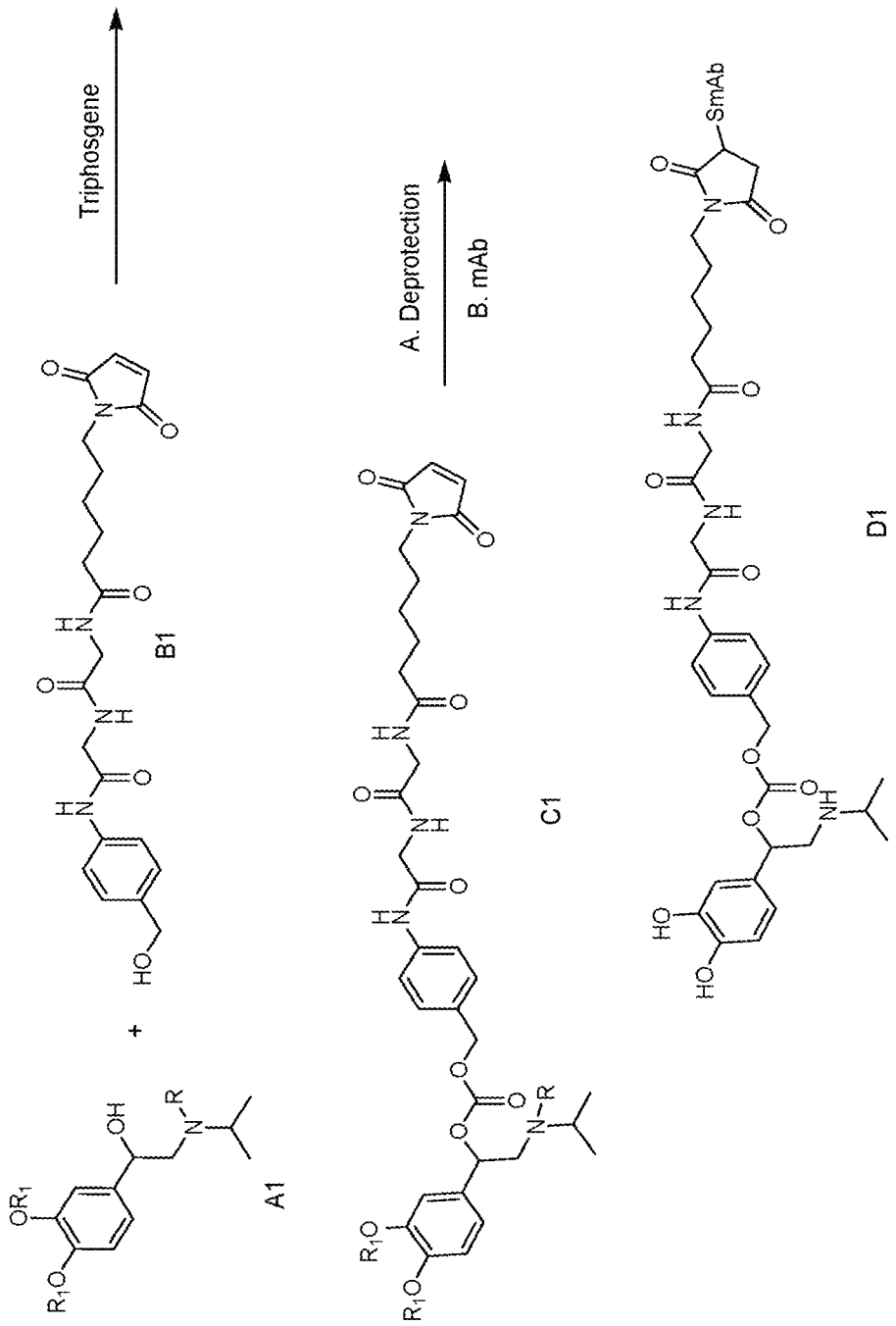
FIG. 5B is a chemical Scheme for preparing the conjugate of Formula IV.

FIG. 5B depicts Scheme 2, which describes an exemplary synthesis of Formula IV. As shown in scheme 2, isoproterenol may be protected on phenolic hydroxyl groups and secondary amine by methods familiar to those in the art, to form intermediate A1. The linker may be assembled with the self-immolating group (para-aminobenzyl alcohol), a simple dipeptide (Gly-Gly) and cysteine attachment. In this case a water solubilizing group may not be employed and instead the secondary alcohol of isoproterenol is employed for the attachment, leaving the secondary amine unreacted. The unreacted secondary amine may provide the required solubility of ADC. Intermediate A1 may be treated with a carbonyl source such as triphosgene, diphosgene, phosgene, carbonyldiimidazole, and the like, in the presence of B1 or subsequently reacted with B1 resulting in intermediate C1. Intermediate C1 may be deprotected as methods known in art and conjugated with the antibody. In some implementations the antibody is an anti-beta adrenoceptor antibody or an anti-trace amine associated receptor 1 antibody.

Formula V is an exemplary schematic of the olanzapine ADC:

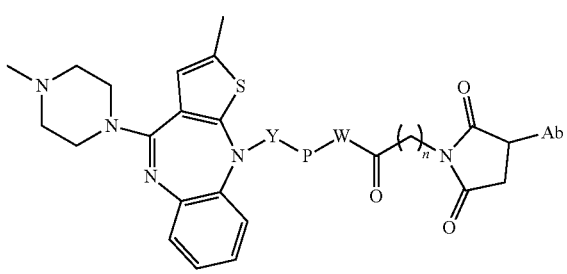

(V)

in which Ab is the antibody and in which the linker comprises Y, which is a self-immolating group bound to the isoproterenol, P, which is a protease sensitive peptide, W, which is a water solubilizing group, and an N-alkyl-succinimide bound to the water solubilizing group and the antibody (Ab), wherein n is 1 to 8.

Formula VI is an exemplary schematic of the methyldopa ADC:

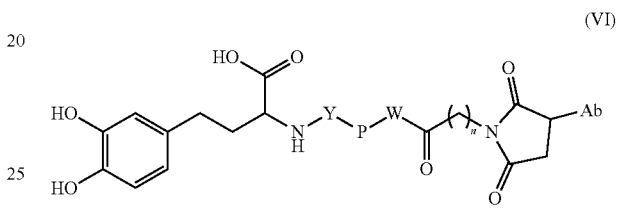

(VI)

in which Ab is the antibody and in which the linker comprises Y, which is a self-immolating group bound to the isoproterenol, P, which is a protease sensitive peptide, W, which is a water solubilizing group, and an N-alkyl-succinimide bound to the water solubilizing group and the antibody (Ab), wherein n is 1 to 8.

In some implementations, the methods described herein further include first determining a number of PBMC by a cell viability assay based on a luminescence measurement prior to the administering and a second determining of the number of PBMC by the cell viability assay based on the luminescence measurement after the administering. The cell viability assay may be one of the aforementioned assays. For example, the luminescence measurement may be taken by a kit such as CellTiter-Glo® (Promega, USA), or a similar kit. The luminescence may be directly proportional to the number of cells in the sample. The luminescence may be produced by a luciferase reaction. The cell viability may be measured by ATP quantitation. In some implementations, the cell viability may be based on a fluorescence measurement such as with CytoPainter® (Abcam, UK). Other exemplary kits which may be employed include ApoTox-Glo™, CellTox™ Green Cytotoxicity Assay and CytoTox-ONE™ (Promega, USA), Vybrant® Cytotoxicity Assay Kit and the LIVE/DEAD® Viability/Cytotoxicity Kit for mammalian cells (Molecular Probes, USA), FluoForte® Calcium Assay kit (Enzo Life Sciences Inc., USA) In some implementations of the method, the number of PBMC is reduced by 5% to 60%, 10% to 55%, 15% to 50%, 20% to 40%, or 25% to 35% relative to a number of PBMC in the leukemia patient prior to administering the drug.

The examples below are intended to further illustrate aspects of the method described herein and are not intended to limit the scope of the claims.

EXAMPLE

Material and Methods
Biological Reagents

General biological reagents not listed elsewhere (e.g. buffers) were purchased from Sigma-Aldrich and Roth (Germany) and were of the highest purity.

Library and Compounds

The compound library used in the screening activities comprised the ENZO FDA SCREEN-WELL® FDA approved drug library V2 (ENZO, BML-2843-0100). This compound library contains 786 compounds that can be used for diverse drug discovery in the several therapeutic areas, with known bioactivity and greater degree of drug-likeness as well as recently approved FDA compounds are also included. Each compound was at a concentration of 10 mM in 100% DMSO. Repurchased compounds were in solid form from Sigma-Aldrich (R-(—)-Apomorphine hydrochloride hemihydrate, Melphalan and Hexachlorophene), Absource Diagnostics GmbH (Doxorubicin, Epirubicin HCl, Daunorubicin HCl, Lapatinib (GW-572016) Ditosylate and Idarubicin HCl), or Tocris (isoproterenol, olanzapine, and methyldopa).

Ethics of Experimentation and Blood Withdrawal:

The institutional research board at King Abdulla International Medical Research Centre/King Abdulaziz Medical City approved the study. All blood samples from healthy volunteers, CLL, CML and AML patients was obtained from patients after discussing the project with them and then signing an informed consent. 40 mL-50 mL blood was withdrawn from each individual by trained phlebotomist nurse following the NGHA standard rules.

PBMC Purification and Cell Induction

Whole blood was taken from experimental group patients and control group patients. The collected blood was transferred to EDTA tubes with a 5 mL pipette and a pipette aid and then to each EDTA tubes corresponding 50 ml centrifuge tubes. All the blood from one patient was placed into 1 tube (50 mL) and an equal volume of PBS was added to the 50 mL centrifuge tube. The sample was then mixed by either inverting the tube or pipetting up & down. The blood was transferred into tow 50 mL leucosep tube and centrifuged at room temperature (18-20° C.) for 15 minutes at 800×g with the brake turned off and acceleration at 2/deceleration at zero. After centrifugation, the white cell interface (buffy coat) was removed by pasture pipette and transferred to the new appropriately labelled 50 ml centrifuge tube. 25 mL PBS was added to the white cell interface (buffy coat) and the mix was centrifuged for 10 minutes at room temperature at 400×g with the brake off and acceleration at 4 & deceleration at 2. The supernatant was discarded from the pellet carefully in an appropriate manner. The pellet was washed another time with 20 mL by centrifugation for 5 minutes as above. The pellet was re-suspended in 5 mL and cells were counted using V-Cell. The cells were then either used directly as fresh for screening or frozen in liquid nitrogen in 10% DMSO/RPMPI media until use.

For cell induction, a 6-well plate was seeded at a concentration of 2.106 cell per well in complete media (RPMI-1640 plus 10% FBS, 1% Penicillin Streptomycin, 1% L-glutamine, 1% MEM Non-Essential Amino Acids Solution). Incubation overnight followed by induction of the cells by adding 0.3M sorbitol to the culture media. After 30 minutes of incubation the media and cells were collected and centrifuged at 500×G for 10 minutes. Supernatant was discarded and the cell pellet was resuspended in cell-lysis buffer and processed for p38 quantification or frozen at −80° C. for later use.

Primary Screening (Assessment of compound cytotoxicity) and Hit follow-up Screening The assay used for TitreGlo (Promega) to measure cell viability based on the ATP production. The assay has been as a standard in many drug discovery research projects due to its sensitivity. The assay was developed in a 384-well plate with 2500 cell/well in 50 uL total volume. Alternatively, the assay could be developed in a 96-well plate with 10,000 cells/well. To calculate the Z' of the assay we considered the following as control: Negative Control (High control)=x % DMSO in column XX and the positive Control (Low control)=no cells as 100% inhibition. % Inhibition was calculated relative to the high control (0% Inhibition) and the low control (100% Inhibition). Z' as a statistics factor was calculated as follows:

$$Z' = 1 - \frac{3*(\sigma_L + \sigma_H)}{(\mu_L - \mu_H)}$$

σ=standard deviation
μ=average
L=% inhibition low control
H=% inhibition high control The Z' of the assay should be between 0.5-1. Assays with Z' less than 0.5 would not be used.

Assay ready compound plates for the 10 μM medium-throughput screening activities were prepared by the Fraunhofer-IME SP in Hamburg and subsequently shipped to KAIMRC for screening using the primary cells. Each compound from the ENZO FDA SCREEN-WELL® FDA approved drug library V2 (0.10 μl in 100% DMSO) was transferred to white, 384-well, PS, Cellstar plates (Greiner Bio-One) using the Echo® Liquid Handler (Labcyte Inc.). Each plate contained one column for the High/Low Controls. The Low Control (1% DMSO v/v in column 23, no cells) and the High Control (final 1% DMSO v/v in column 24, with cells) were employed to calculate the Z' for each assay plate. Upon thawing a suitable number of vials containing the primary cells in RPMI-1640 medium containing 2 mM glutamine, 100 U/mL penicillin G, 100 mg/mL streptomycin and 10% fetal calf serum (FCS), they were counted in RPMI-1640 medium before seeding into 384-well plates (20 μL) at a density of (1,000 cells/well) in the assay ready plates containing 0.10 μl compound in 100% DMSO or DMSO alone for the High/Low Controls and incubated at 37° C. in the presence of 5% $CO_2$. At 24 h post seeding, baseline growth was assessed using a control plate and CellTiter-Glo (CTG) reagent (Promega Corporation). Briefly, 20 μL/well of CTG detection mix was added and plates were read using an EnVision Multimode plate reader (PerkinElmer) after 10 min incubation in the dark. The raw luminescence signal was normalized in ActivityBase XE with outliers in control wells eliminated according to the 3-sigma method to yield percentage of cell viability by using the High Control (HC) containing cells in 1% DMSO v/v (Carl Roth) and the Low Control containing 1% DMSO v/v (Carl Roth). All Medium-Throughput Screening experiments were performed in duplicate for each patient. Those compounds that yielded >50 cytotoxicity were classified as "Hits" and subsequently screened in dose-response format in 11-point dose-responses in duplicates. Assay ready plates containing the Hit compounds in dose-response format were prepared in a manner similar to that for the 10 μIM screening described above. The raw luminescence signal was processed using Graph Pad Prism (Graph Pad Software Inc.) with outliers in control wells eliminated according to the 3-sigma method. The dose-response curves were analyzed using a 4 parameter sigmoidal fit to obtain plausible results in the case non-sigmoidal dose-response curves.

Results
Developing and Optimizing the TiterGlo assay

Figure 6:
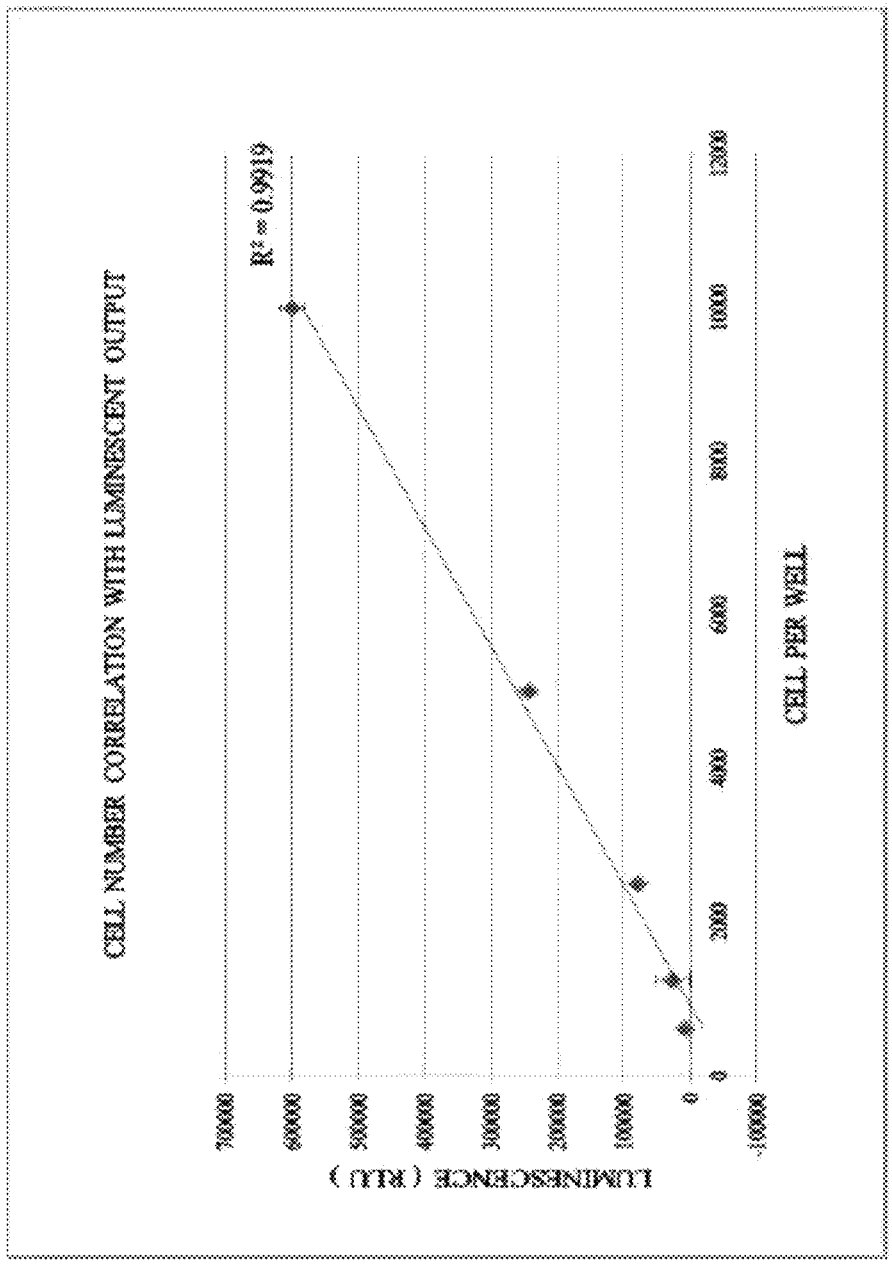
FIG. 6 is a cell growth curve of PBMC cells.

To screen for efficacy of marketed drugs, we first developed the TitreGlo assay using PBMC prepared from healthy volunteer. As described in Material and Methods section herein, the different number of cells were incubated in 384 well plate in total media volume of 25 ul. The cell growth was measured after 24 hr using TitreGlo. As shown in FIG. 6, the growth signal increased by increasing cell number and the assay gave an R2 equal to 0.9912 determining that the assay is of good quality. For the drug screening in 384 well plates, 2500 cell/well were seeded.

Figure 7:
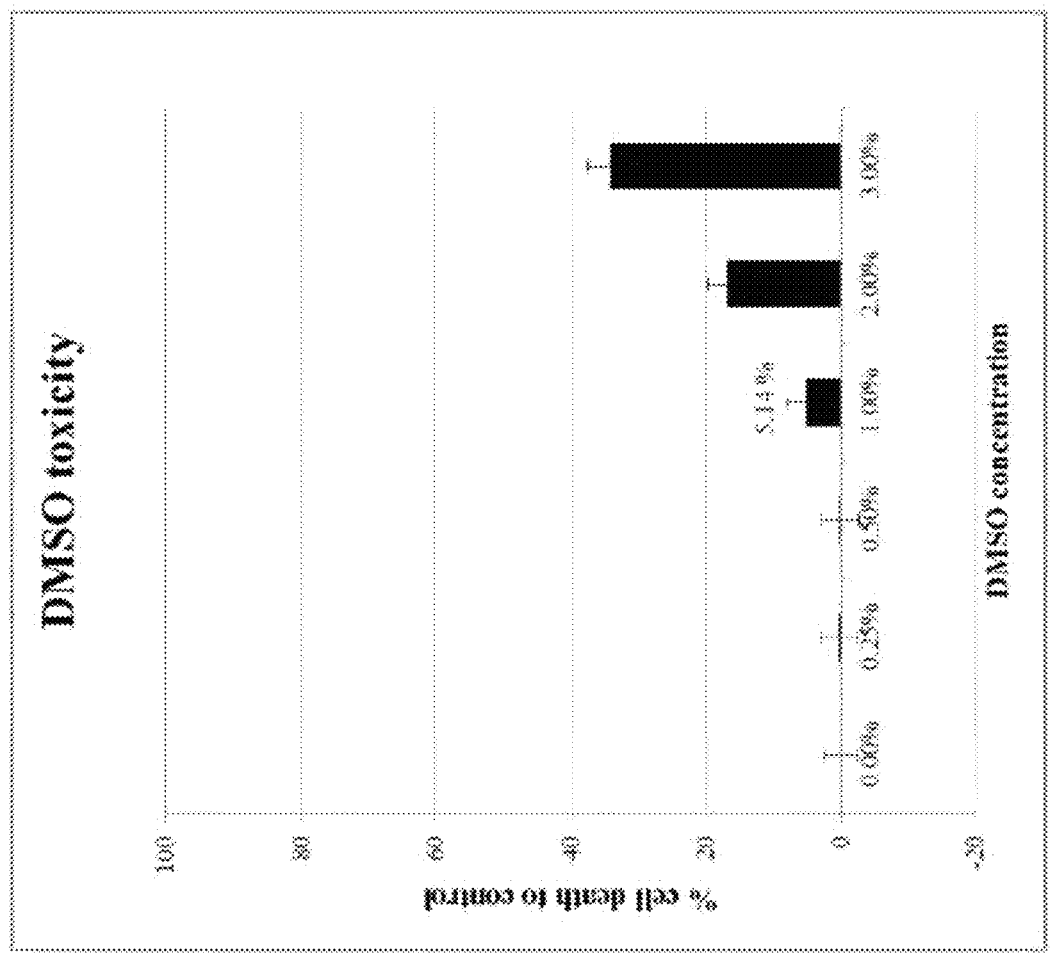
FIG. 7 is a bar graph of cytotoxicity from DMSO in PBMC cells.

Next the assay tolerability to DMSO was tested to determine the maximum DMSO concentration that is not toxic more than 5% to the cells. In this regard, we incubated 2500 cell/well in 25 uL total volume of media and DMSO. The DMSO concentration varied from 0.25% to 10%. After 24 hr incubation, the growth curve was measured by TitreGlo. As shown in FIG. 7, increasing the DMSO induces cell death. At 1% final DMSO concentration the cell death was less than 5% which is upper limit of total DMSO volume that can be used in the assay. In this regard, the DMSO did not exceed 1% in the assay.

Figure 8:
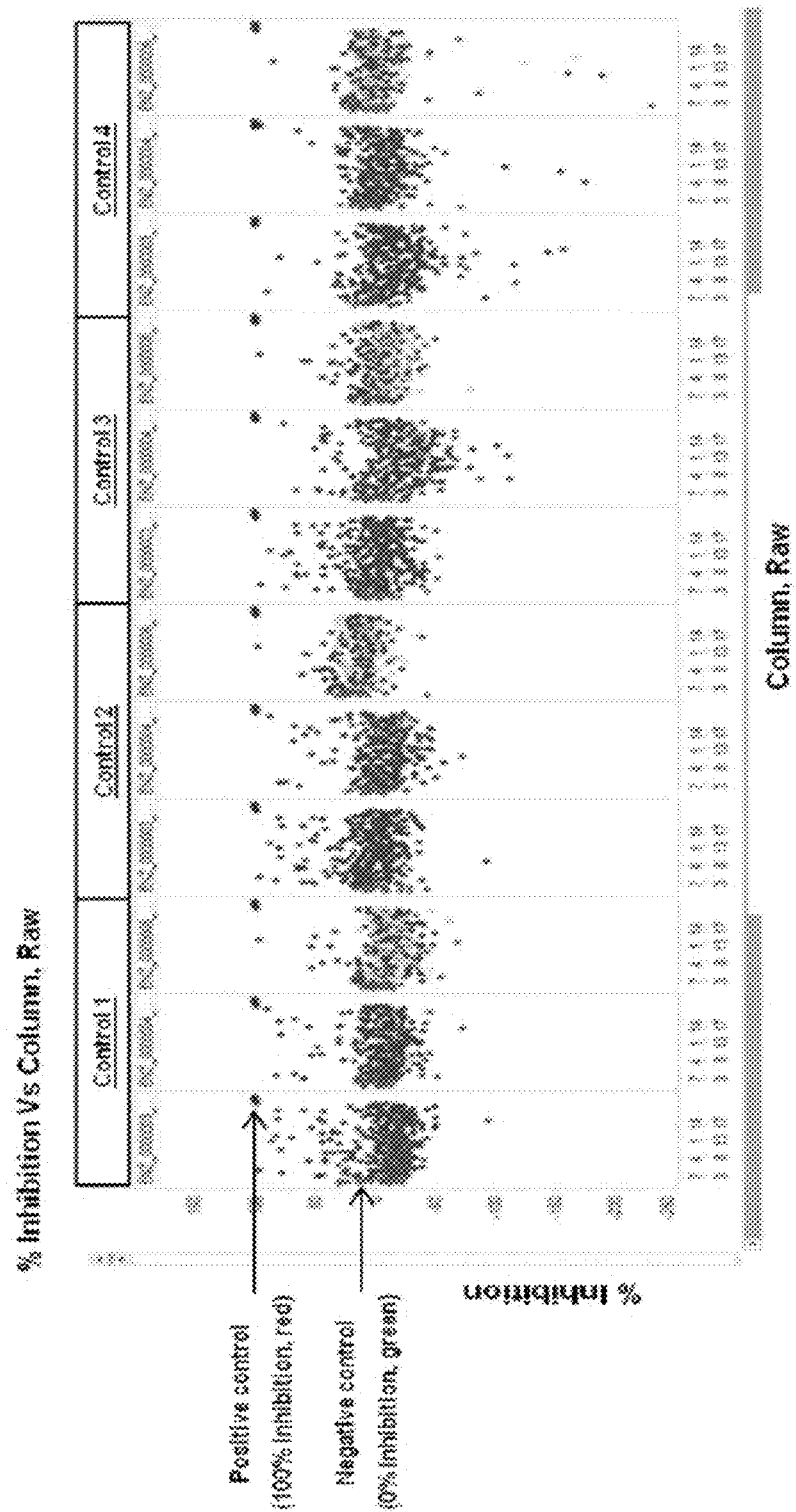
FIG. 8 is a graph of cytotoxicity data from screening of patients' primary PBMC cells with marketed drug library from 4 healthy patients (control samples)

Screening Marketed Drug Set in PBMCs
Screening Using PBMCs from Healthy Volunteers, Controls While the assay performed as expected, PBMC were prepared from 4 different donors for further tests. The Screen-Well FDA approved drug library was screened, which contains 780 approved drugs. The compound plates were prepared by Fraunhofer Institute. Each well plate contained 0.25 uL to give final concentration of compound in assay 10 uM. The final DMSO concentration in the assay plate was 0.1% of total volume. As indicated the FIG. 8 the signal to noise of positive and negative control was able to be differentiated in all four controls indicating the assay is sufficiently sensitive to be used in patients' sample. The average of all four control samples was then calculated and used to determine the positive "hits" in patients' samples.

Screening Using PBMCs from Leukemic Patients

Figure 9A:
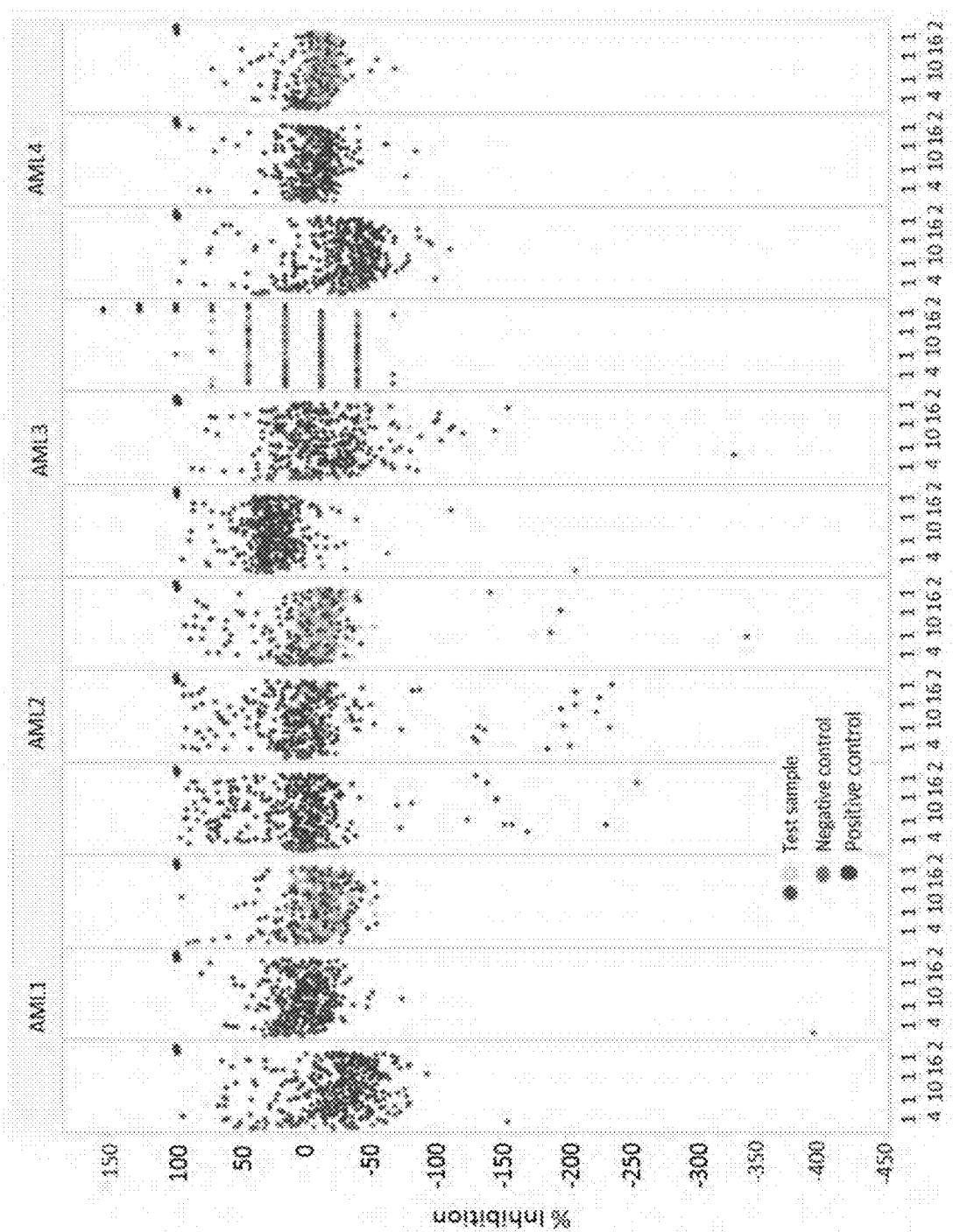
FIG. 9A is graphic of cytotoxicity data from screening of patients' primary PBMC cells with marketed drug library from 4 AML patients.
Figure 9B:
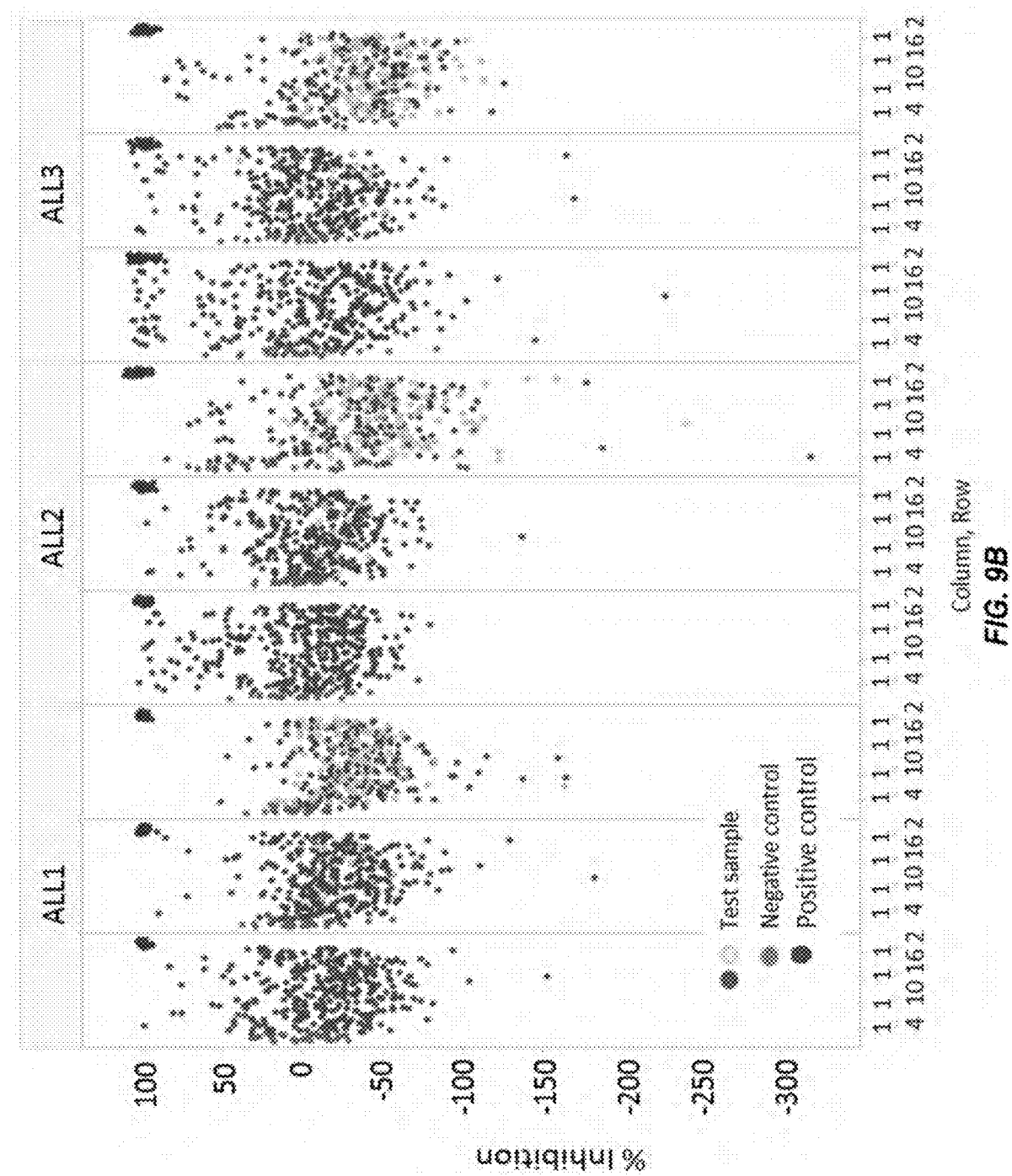
FIG. 9B is graphic of cytotoxicity data from screening of patients' primary PBMC cells with marketed drug library from 3 ALL patients.
Figure 9C:
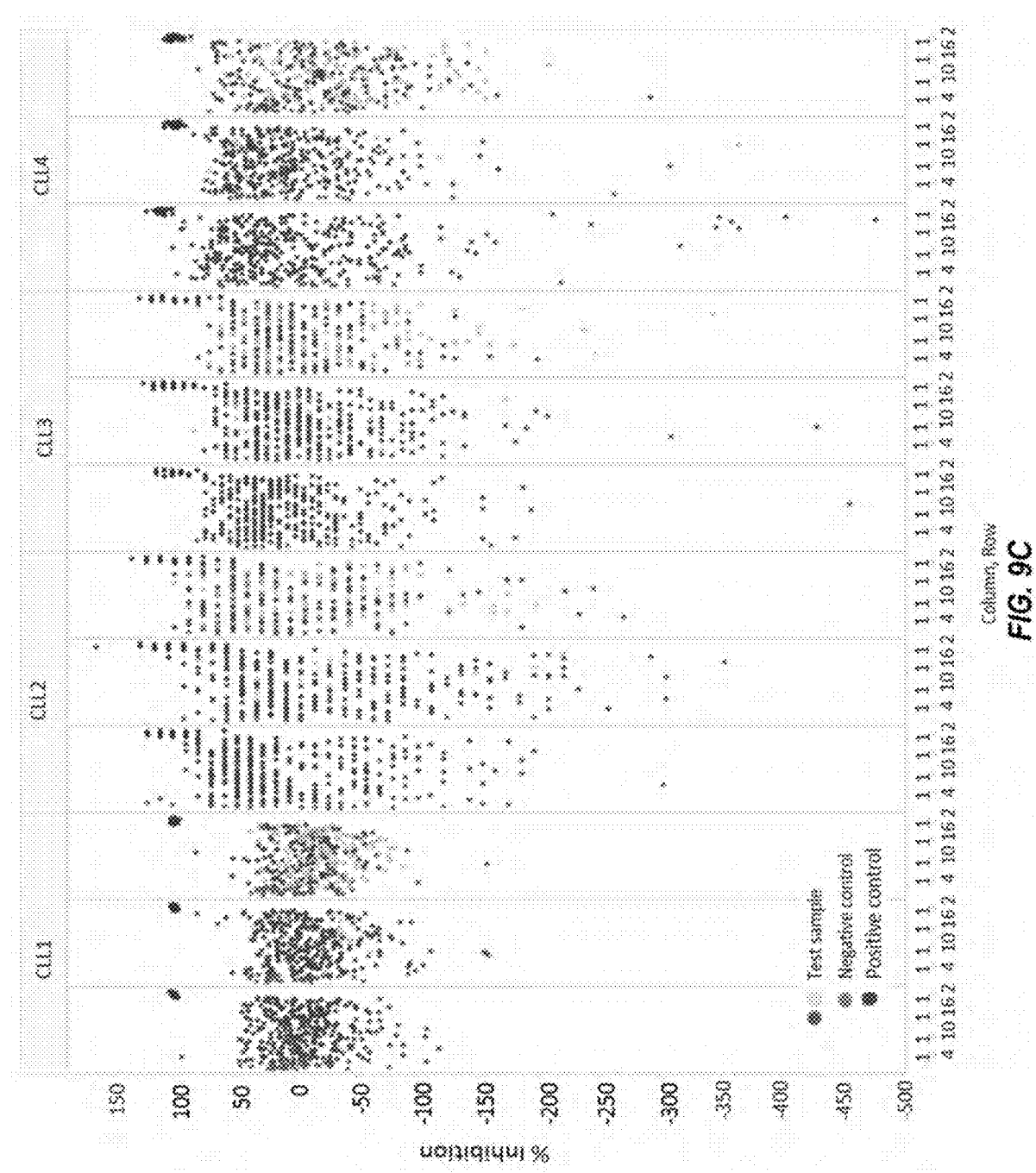
FIG. 9C is graphic of cytotoxicity data from screening of patients' primary PBMC cells with marketed drug library from 4 CLL patients.
Figure 10A:
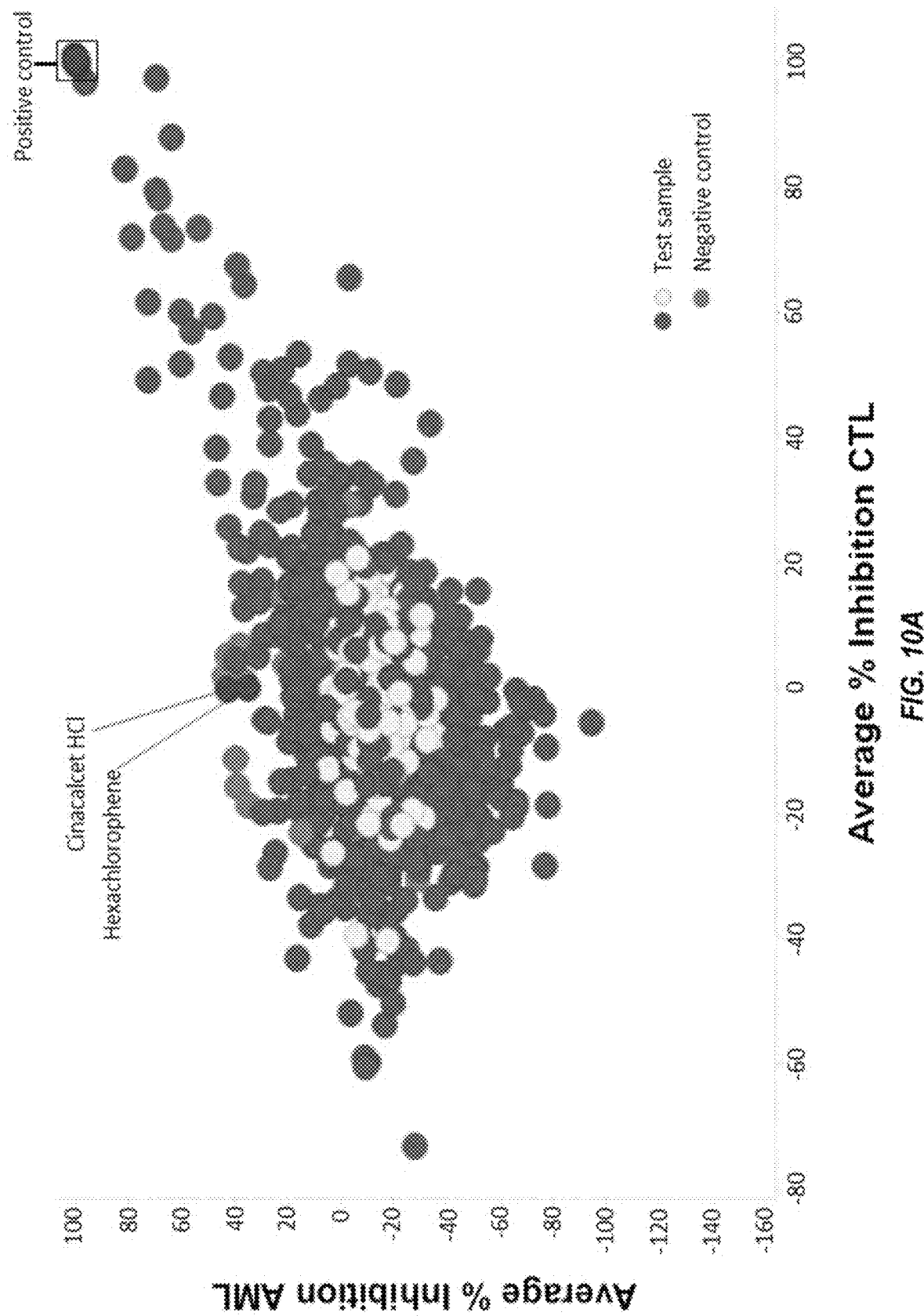
FIG. 10A is a graph correlating the average % inhibition of AML in patients and the average % inhibition of the control individuals.
Figure 10B:
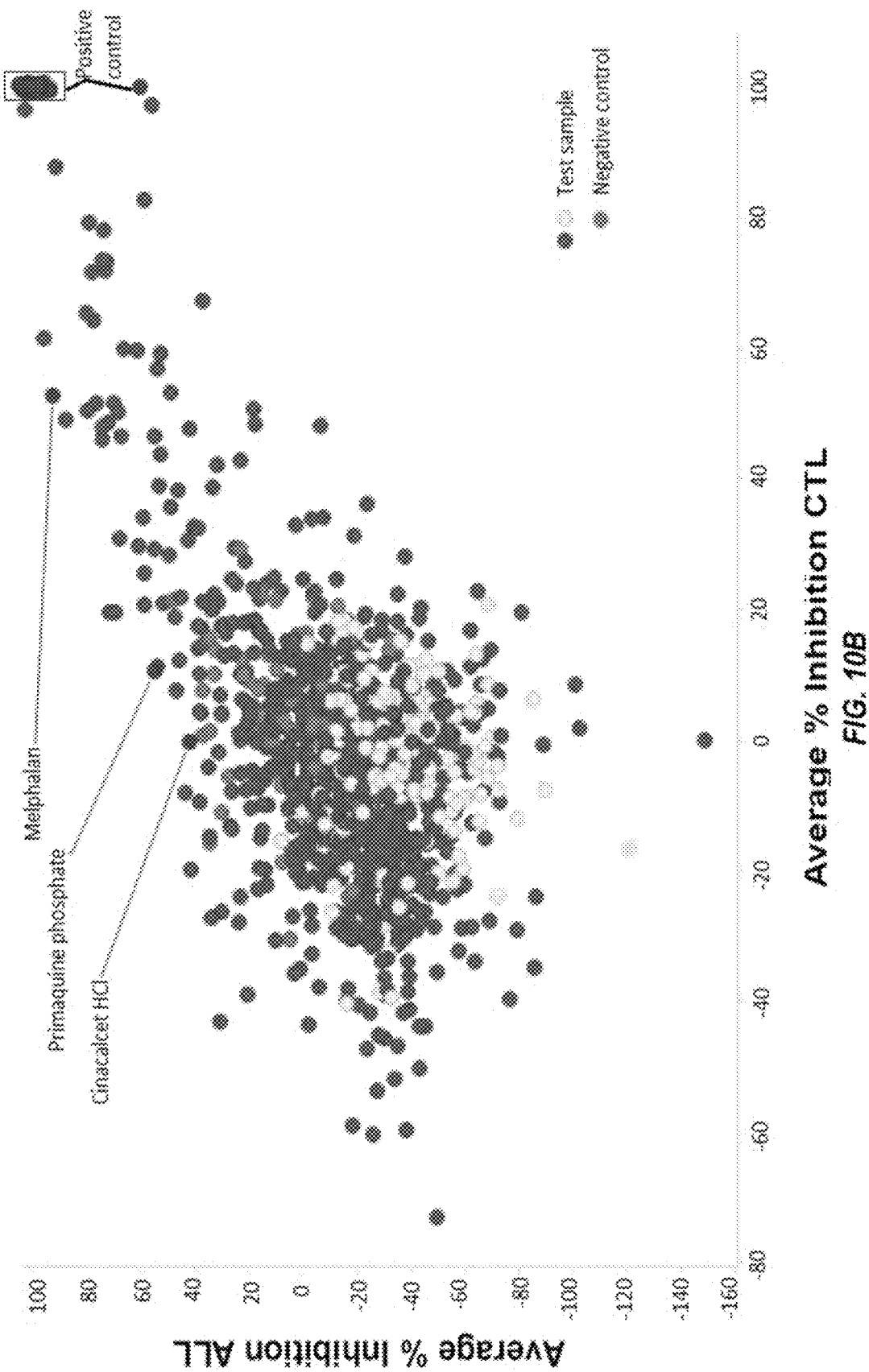
FIG. 10B is a graph correlating the average % inhibition of ALL in patients and the average % inhibition of the control individuals.
Figure 10C:
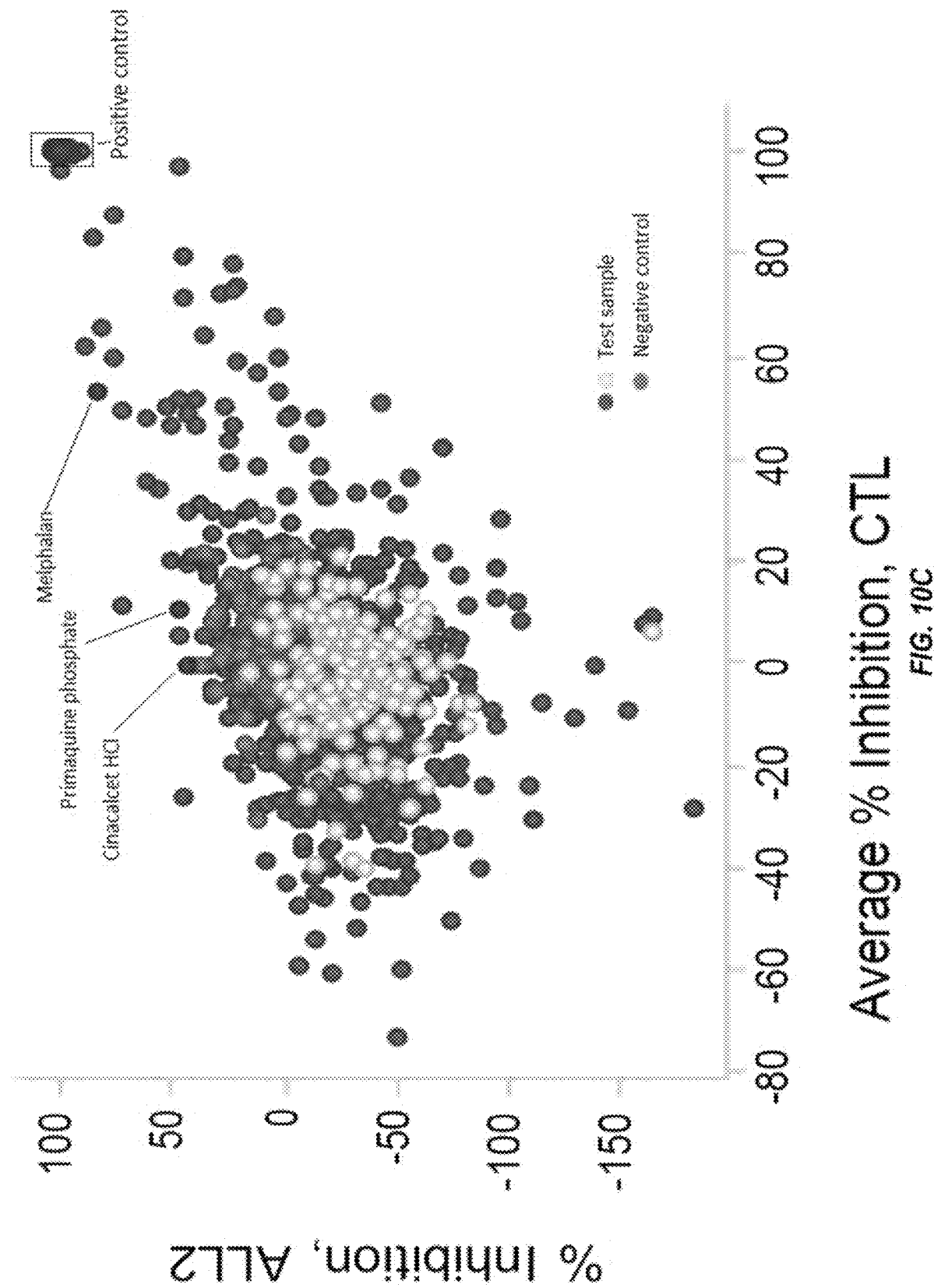
FIG. 10C is a graph correlating the % inhibition of ALL in a first patient and the average % inhibition of the control individuals.
Figure 10D:
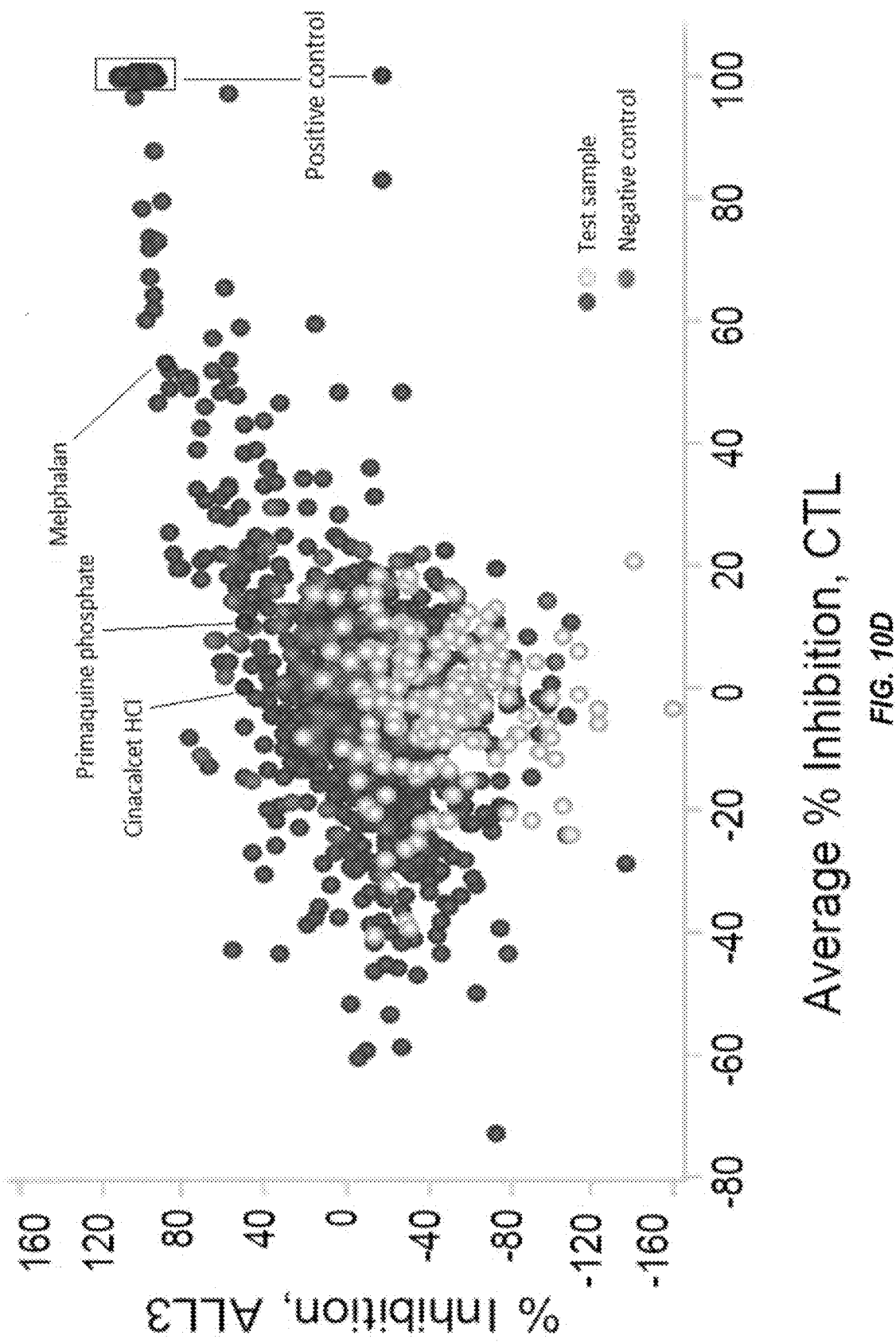
FIG. 10D is a graph correlating the % inhibition of ALL in a second patient and the average % inhibition of the control individuals.
Figure 10E:
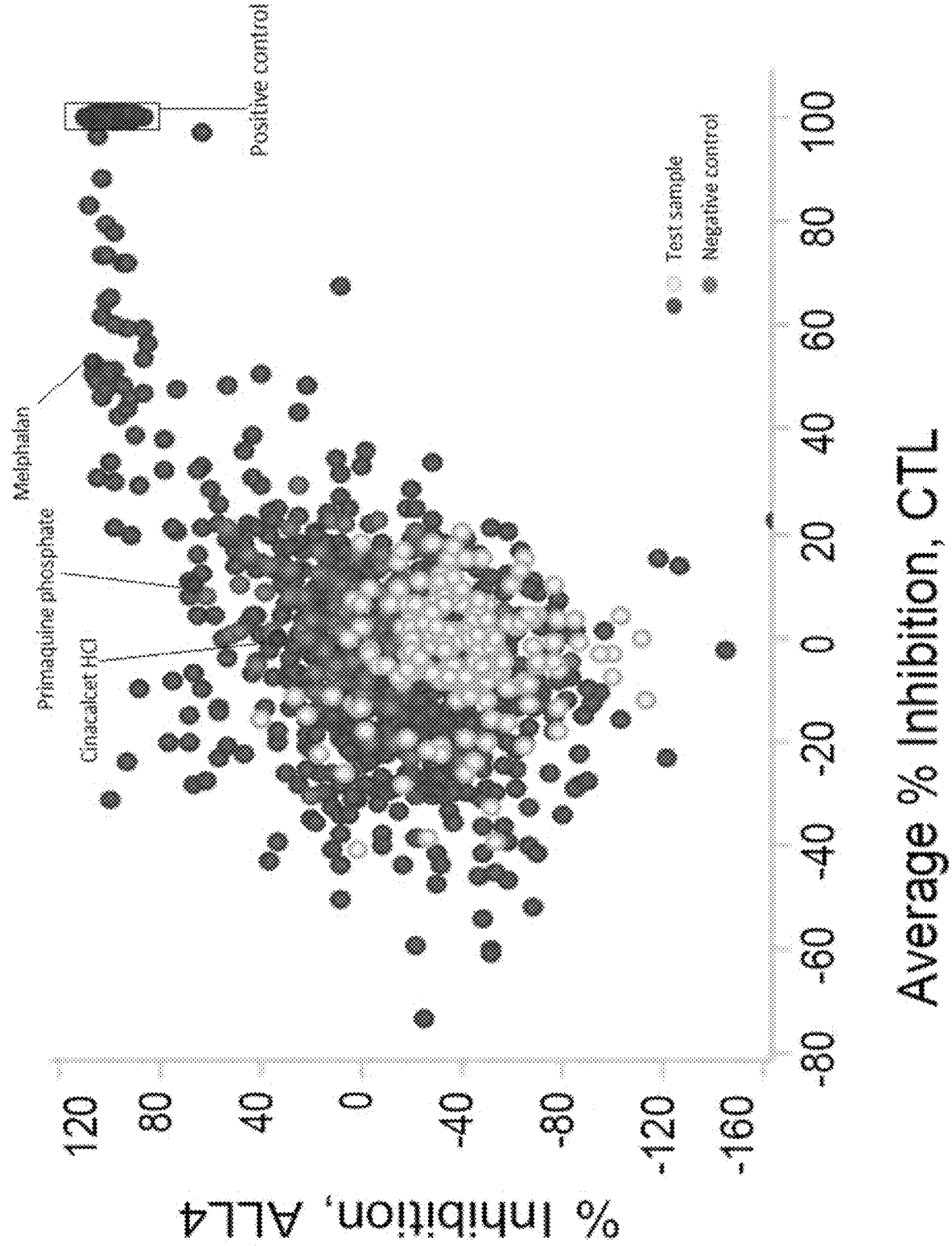
FIG. 10E is a graph correlating the % inhibition of ALL in a third patient and the average % inhibition of the control individuals.
Figure 10F:
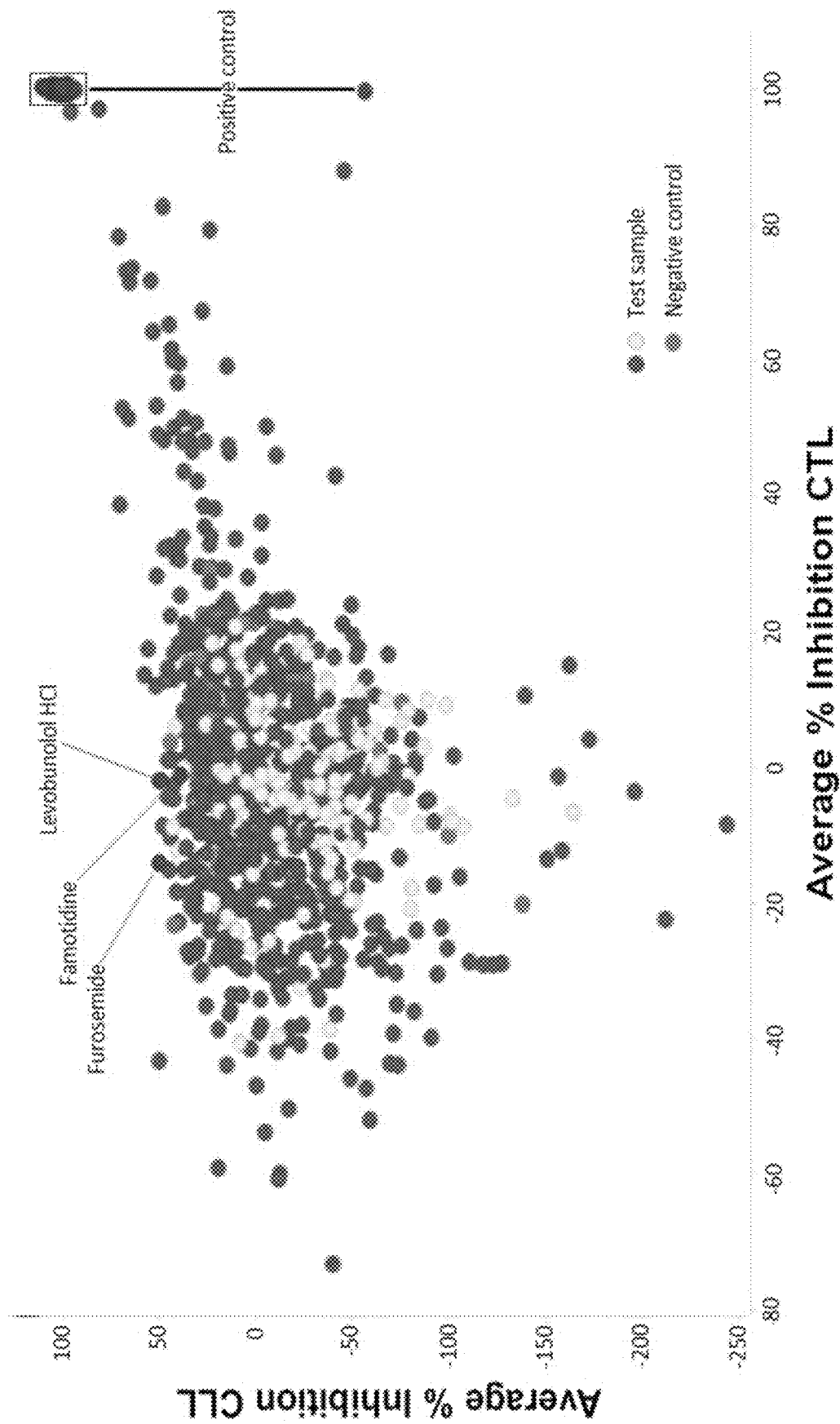
FIG. 10F is a graph correlating the average % inhibition of CLL in patients and the average % inhibition of the control individuals.
Figure 10G:
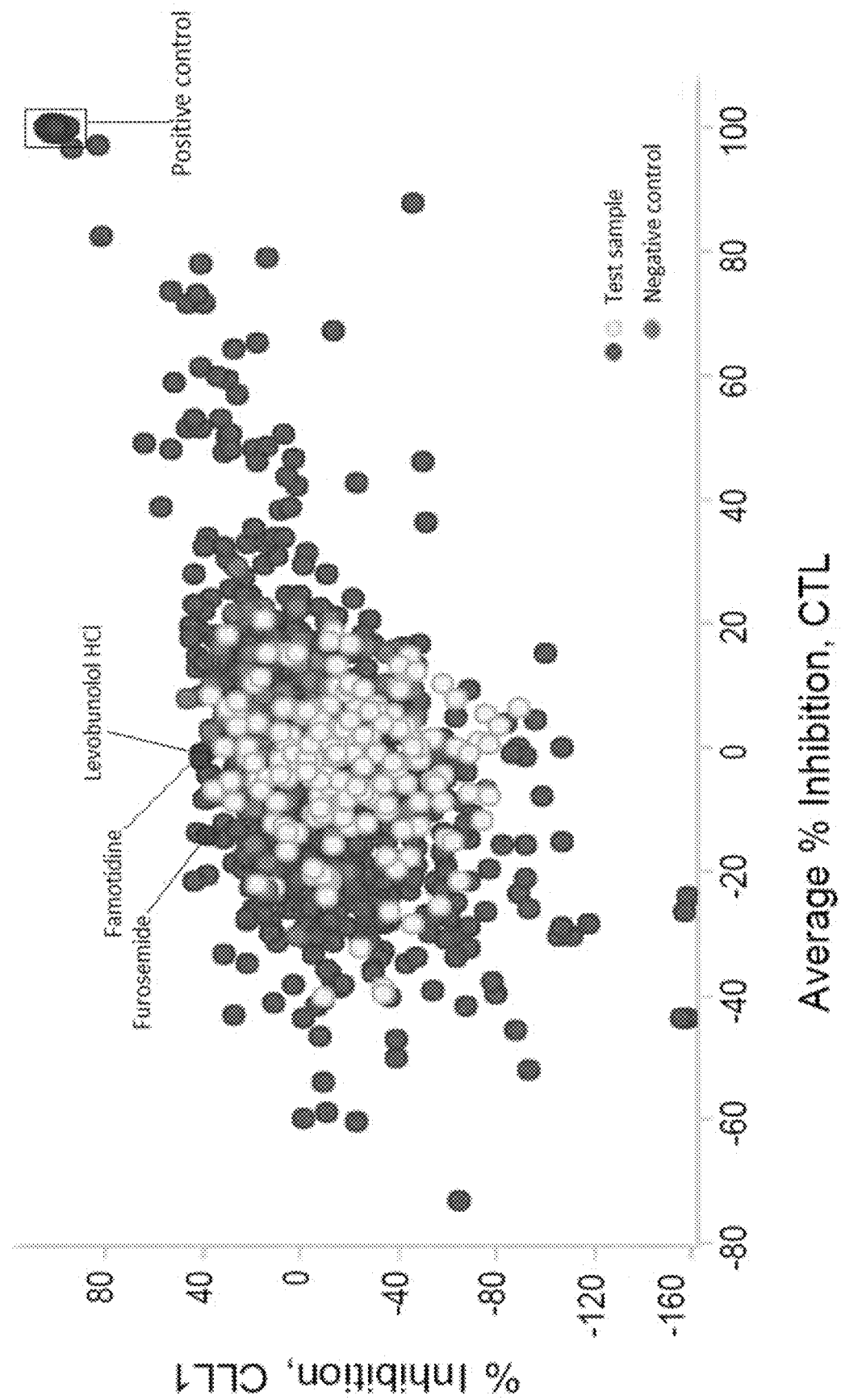
FIG. 10G is a graph correlating the % inhibition of CLL in a first patient and the average % inhibition of the control individuals.
Figure 10H:
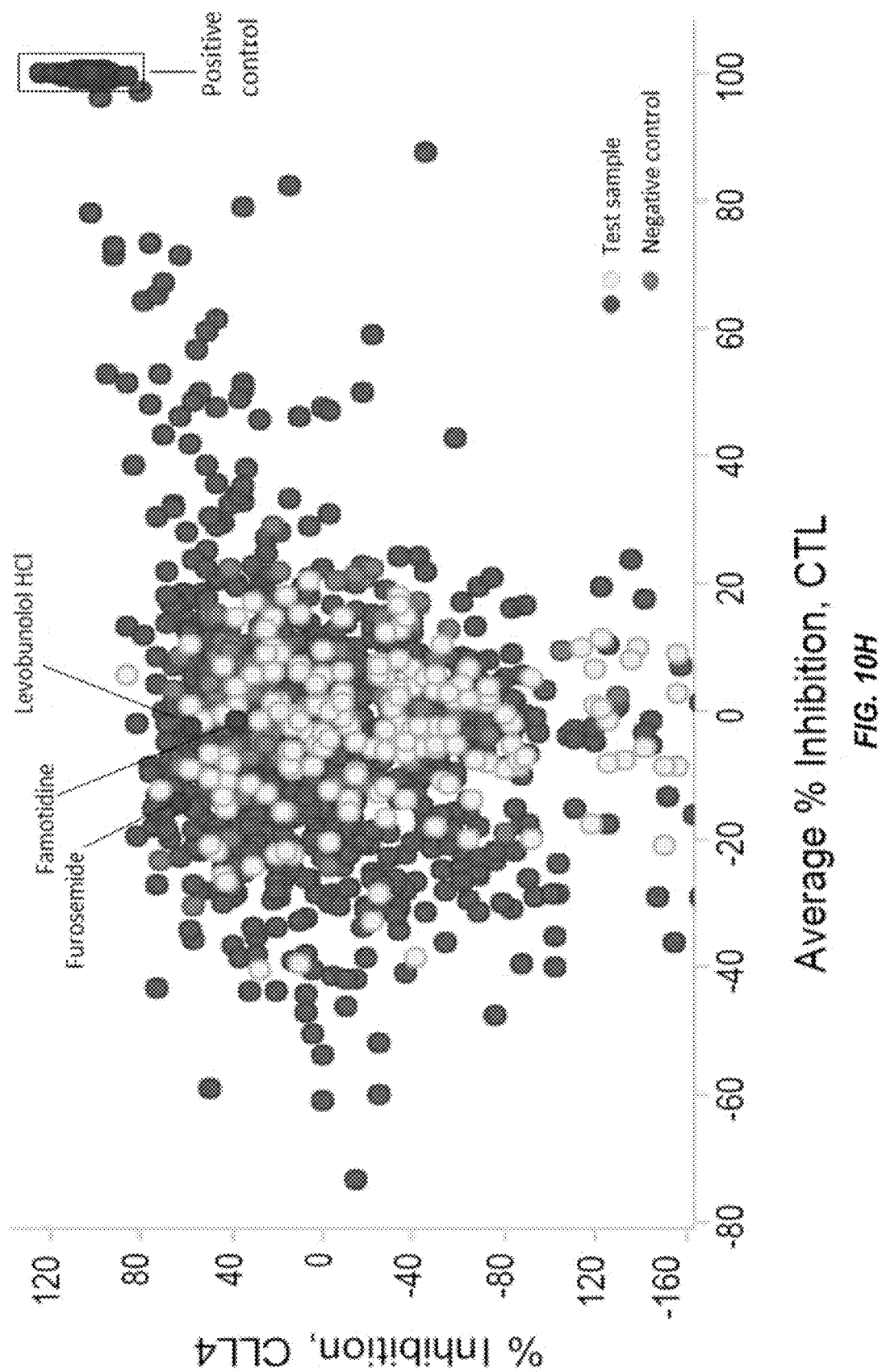
FIG. 10H is a graph correlating the % inhibition of CLL in a second patient and the average % inhibition of the control individuals.

After determining the parameter condition of the TitreGlo assay in 384 and screened control samples, it was then used to screen PBMCs prepared from 4 AML patients samples (FIG. 9A), 3 ALL patients samples (FIG. 9B), and 4 CLL patients samples (FIG. 9C). The average inhibition (cell death) was calculated for each well/plate in comparison to the 100% inhibition (well that did not contain any cells and considered as positive control).

Figure 11:
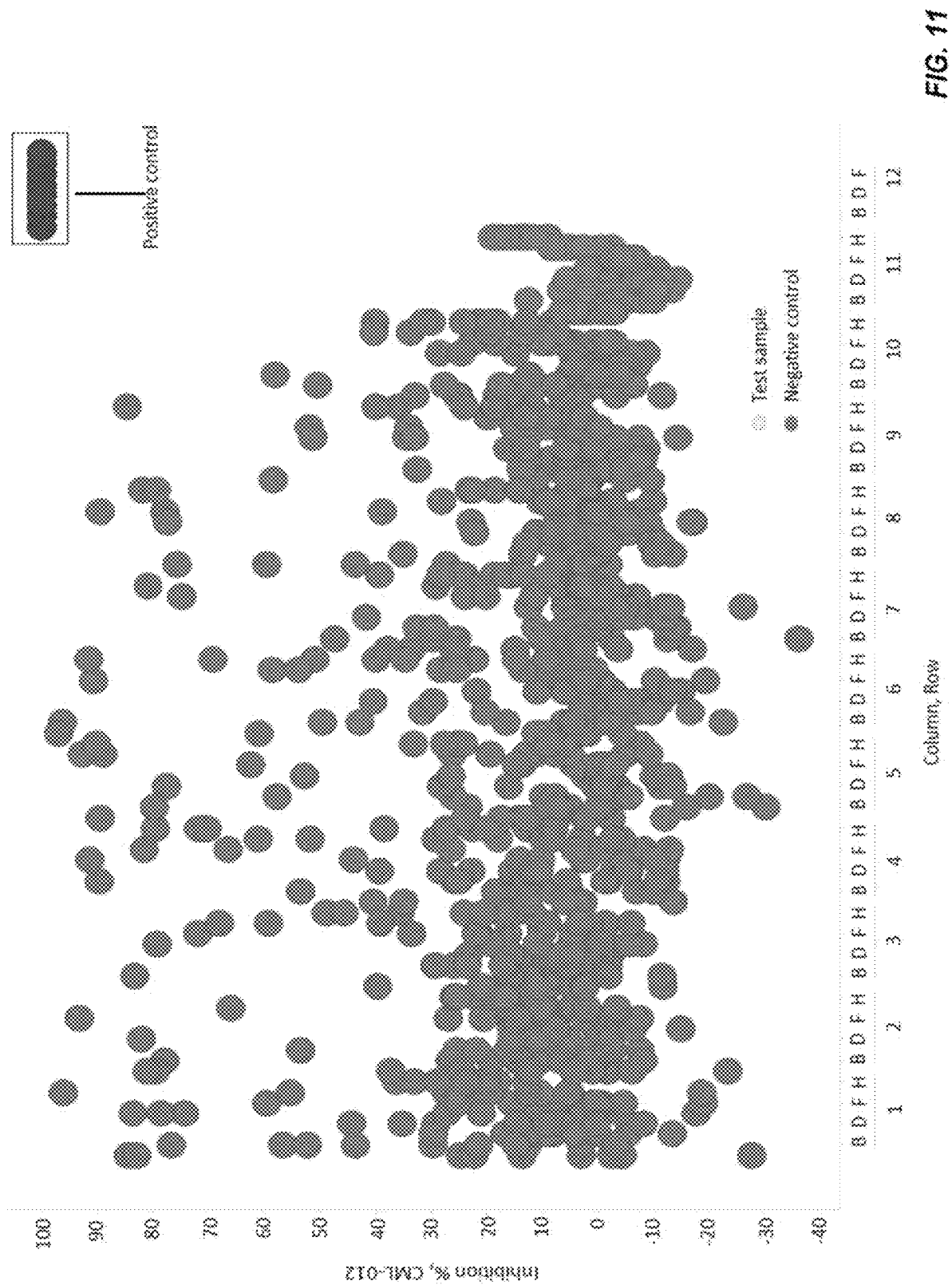
FIG. 11 is a graph correlating the average % inhibition of CML patients and the average % inhibition of the control individuals.

As shown in the FIG. 11 there was variability when screening the patient's samples compared to the control plates (healthy donors). It may be due to the fact that the signal was very low in few patient samples. Also we noticed that the patient samples in contrast to control, sometime they make aggregate and need to be processed very carefully to ensure that the cell number in each well is the same. The average for each patient samples were calculated. For AML patient samples, the plate number 3 of patient three was ignored as there was an issue of dispensing.

Identifying the Positive Hits

The average inhibition of all samples, control and patients were calculated and then plotted.

Each average patient samples were plotted against average of the control samples to identify the positive hits. The plots are shown in FIG. 10A-FIG. 10H and FIG. 11. Any compound showing 30% inhibition in patients' samples compared to control samples was considered as positive hits. In total 56 compounds were identified as positive hits from all patients samples. These hits were further tested in curve points (dose response curve).

Samples from 4 patients were screened against the FDA approved drug library where the Negative Control (High control) contained cells treated with DMSO and the Positive Control (Low control) were based using no cells. The screening was carried out in 96 well plates. The raw luminescence counts were normalized and the % Inhibition was calculated relative to the high control (0% Inhibition) and the low control (100% Inhibition). Example data for CML-012 are shown in FIG. 11. The signal window in FIG. 11 is sufficient for the active hits distributed randomly in the assay plates.

Table 1 summarizes all the positive hits that showed more than 30% inhibition of the PBMCs growth prepared from leukemic patients compared to control cells. As shown in the table, hits can be classified into three categories as follows: Drugs that are already used in the clinic as antileukemic agents, Drugs that have been reported to effect leukemic cells and third previously unknown target drugs that were discovered to kill at 30% more of at least one category of leukemic PBMC.

TABLE 1

Positive hits of drug that killed PBMCs from at least one leukemic category 30% or more compared to control

| | Name | % Inhibition, CML | | % Inhibition, CLL | | % Inhibition, AML | | % Inhibition, ALL | | |
|---|---|---|---|---|---|---|---|---|---|---|
| | | Average | STD | Average | STD | Average | STD | Average | STD | |
| 1 | Cytarabine | 58.8 | 18.8 | 26.6 | 10.9 | 66.1 | 17.2 | 49.2 | 11.7 | Approved drugs for leukemia |
| 2 | Daunorubicin HCl | 67.6 | 15.8 | 65.5 | 17.2 | 64.0 | 9.2 | 78.4 | 19.2 | |
| 3 | Doxorubicin HCl | 36.7 | 15.0 | 67.2 | 34.9 | 73.6 | 13.7 | 72.6 | 13.6 | |
| 4 | Idarubicin HCl | 43.5 | 58.2 | 54.8 | 11.7 | 79.0 | 12.0 | 73.5 | 18.0 | |
| 5 | Ivermectin | 79.3 | 21.6 | 66.0 | 27.5 | 60.2 | 4.5 | 70.4 | 26.4 | Drugs known to have an effect on leukemia |
| 6 | Apomorphine HCl Hemihydrate | 89.4 | 4.0 | 27.9 | 58.8 | 39.5 | 0.7 | 37.3 | 51.8 | |
| 7 | Auranofin | 94.9 | 3.8 | 96.0 | 3.2 | 96.7 | 1.8 | 102.9 | 2.9 | |
| 8 | Lapatinib Ditosylate | 76.6 | 15.5 | 6.9 | 7.2 | −76.1 | 112.0 | 35.1 | 16.8 | |
| 9 | Disulfiram | 92.4 | 6.7 | −45.4 | 0.1 | 64.0 | 14.1 | 91.5 | 14.1 | |
| 10 | Digoxin | 768 | 15.6 | 30.1 | 40.7 | −33.2 | 58.1 | 32.0 | 90.0 | |
| 11 | Mefloquine HCl | 90.4 | 6.7 | 50.5 | 19.3 | 72.7 | 11.5 | 87.7 | 16.5 | |

TABLE 1-continued

Positive hits of drug that killed PBMCs from at least one leukemic category 30% or more compared to control

| | Name | % Inhibition, CML Average | STD | % Inhibition, CLL Average | STD | % Inhibition, AML Average | STD | % Inhibition, ALL Average | STD | |
|---|---|---|---|---|---|---|---|---|---|---|
| 12 | Silver Sulfadiazine | 75.2 | 41.9 | 81.3 | 1.5 | 69.7 | 37.7 | 56.1 | 7.5 | |
| 13 | (±) Isoproterenol HCl | 65.3 | 12.7 | 39.9 | 11.7 | −211.7 | 395.0 | 61.7 | 40.7 | Noval Drugs that has an effect of more than 30% killing in at least one leukemia category |
| 14 | Olanzapine | 79.5 | 8.7 | −26.5 | 58.5 | 1.8 | 23.1 | 71.8 | 25.0 | |
| 15 | Adefovir Dipivoxil | 63.7 | 14.6 | 43.9 | 3.9 | 72.8 | 14.7 | 96.0 | 6.8 | |
| 16 | Sertraline HCl | 75.8 | 23.9 | 15.4 | 51.8 | 48.9 | 2.0 | 53.0 | 32.7 | |
| 17 | Cyclosporine A | 51.6 | 21.7 | 53.4 | 36.2 | 36.7 | 12.8 | 77.8 | 35.6 | |
| 18 | Pimozide | 69.0 | 27.8 | 39.5 | 15.3 | 42.3 | 6.6 | 58.8 | 27.3 | |
| 19 | Loperamide HCl | 69.3 | 30.3 | 16.3 | 15.2 | 18.5 | 6.5 | 54.9 | 29.4 | |
| 20 | Flecainide Acetate | −1.0 | 14.8 | 50.2 | 45.4 | 13.0 | 3.2 | −18.3 | 15.8 | |
| 21 | Dobutamine HCl | 25.3 | 25.9 | −5.0 | 16.6 | −10.5 | 75.0 | 79.6 | 27.3 | |
| 22 | Epinephrine (L-(−)-Epinephrine-(+)-Bitartrate) | 68.4 | 9.0 | 45.4 | 38.6 | −2.8 | 92.9 | 80.5 | 20.0 | |
| 23 | Imipramine HCl | 13.7 | 36.7 | 57.9 | 39.0 | 1.9 | 24.5 | −6.0 | 12.7 | |
| 24 | Famotidine | 17.1 | 23.7 | 39.2 | 2.4 | 5.3 | 1.5 | 13.4 | 5.2 | |
| 25 | Clemastine Fumarate | 66.4 | 34.0 | 55.6 | 15.1 | 13.5 | 7.1 | 39.1 | 11.7 | |
| 26 | Nifedipine | 4.2 | 31.7 | −10.8 | 54.7 | 7.9 | 26.5 | 74.3 | 26.9 | |
| 27 | Clofarabine | 21.9 | 29.3 | 41.3 | 44.3 | −20.6 | 47.0 | 68.1 | 14.4 | |
| 28 | Furosemide | −38.4 | 29.9 | 50.3 | 18.0 | −39.0 | 16.9 | −31.3 | 5.1 | |
| 29 | Melphalan | 32.5 | 37.7 | 69.6 | 36.0 | 42.1 | 14.7 | 92.9 | 11.6 | |
| 30 | Metronidazole | −17.3 | 40.5 | 31.0 | 72.4 | −25.2 | 8.4 | −23.9 | 2.1 | |
| 31 | Mitoxantrone HCl | 72.6 | 22.7 | 71.1 | 42.8 | 68.8 | 9.2 | 73.7 | 43.5 | |
| 32 | Oxiconazole Nitrate | 61.7 | 24.7 | 12.2 | 53.8 | 8.7 | 3.4 | 25.7 | 23.2 | |
| 33 | Primaquine Phosphate | 40.9 | 9.7 | 16.9 | 20.2 | 19.8 | 14.0 | 54.9 | 10.7 | |
| 34 | Thioridazine HCl | 70.3 | 28.7 | −40.9 | 25.0 | 27.0 | 11.9 | 23.1 | 27.9 | |
| 35 | Butoconazole Nitrate | 58.5 | 26.9 | 44.1 | 31.2 | 46.6 | 10.9 | 40.7 | 35.4 | |
| 36 | Chlorhexidine Dihydrochloride | 59.9 | 47.9 | 70.3 | 18.4 | 26.9 | 4.1 | 53.6 | 33.2 | |
| 37 | Cinacalcet HCl | 63.3 | 23.2 | 28.6 | 42.9 | 43.2 | 14.0 | 41.9 | 8.5 | |
| 38 | Dactinomycin (=Actinomycin D) | 24.4 | 25.1 | 42.9 | 12.2 | 60.4 | 15.7 | 66.5 | 55.6 | |
| 39 | Epirubicin HCl | 5.0 | 32.7 | 64.3 | 16.5 | 67.1 | 11.5 | 74.4 | 45.3 | |
| 40 | Fingolimod | 76.1 | 21.2 | 47.9 | 46.8 | 81.5 | 10.4 | 58.9 | 66.6 | |
| 41 | Fludarabine Phosphate | 19.1 | 36.1 | 17.3 | 13.9 | 21.8 | 5.3 | 53.9 | 28.3 | |
| 42 | Hexachlorophene | 26.3 | 33.3 | −13.5 | 53.4 | 35.0 | 4.6 | 23.0 | 13.6 | |
| 43 | Levobunolol HCl | −32.1 | 33.2 | 49.6 | 13.0 | 1.8 | 8.5 | −8.0 | 3.3 | |
| 44 | Miconazole | 69.9 | 28.6 | −3.3 | 60.1 | 38.1 | 23.4 | −35.1 | 28.1 | |
| 45 | Rifapentine | 76.5 | 18.1 | 12.3 | 43.1 | −3.2 | 12.4 | −3314.5 | 5772.9 | |
| 46 | Rifaximin | 42.3 | 59.3 | −60.2 | 27.4 | −42.8 | 15.4 | −45.4 | 60.4 | |
| 47 | Sunitinib Malate | 65.2 | 33.6 | 40.5 | 21.4 | 56.5 | 23.4 | 54.2 | 38.2 | |
| 48 | Temsirolimus | 7.0 | 38.7 | 26.6 | 37.2 | 1.6 | 31.2 | −6.4 | 25.3 | |

Confirmation of Positive Hits

In order to filter out the true positive hits of the marketed drugs that indicated at least 30% more inhibition in PBMCs from leukemia patients compared to control, testing occurred in dose dependent manner. Compound plates were prepared from the same stock used in the original screening and each compound was tested at 16 concentration point with 100 uM being the highest concentration and the dilution factor was ⅓ between two points.

The TitreGlo was performed as described and the curve for growth inhibition was plotted using activity base to calculate the EC50. After testing all the compounds, data indicated only three of the compounds tested showed promise from the growth inhibition curve. As shown in FIG. 1A-FIG. 1D, FIG. 2A-FIG. 2D and FIG. 3A-FIG. 3B and FIG. 4A-FIG. 4D, the compounds are isoproterenol, olanzapine and methyldopa. To enable confirmation that the effect of these three drugs are reproducible, the drugs were tested by preparing a fresh stock solutions using authentic samples (clean or pure samples). The fresh stock of the three compounds showed similar effects as shown in the described figured herein.

Isoprenaline (INN) or isoproterenol (USAN) (trade names Medihaler-Iso and Isuprel) is a medication used for the treatment of bradycardia (slow heart rate), heart block, and rarely for asthma. In humans, it is a non-selective β adrenoceptor agonist and TAAR1 agonist that is structurally similar to epinephrine (adrenaline). This drug is more effective in killing PBMCs from CLL and CML patients. The EC50 of this drug when tested from freshly prepared stock from solid is 4.8 and 4.4 times higher in control PBMC compared to PBMC prepared from CLL and CML patients respectively. This finding is reproducible and unique and never been reported previously.

Figure 1B:
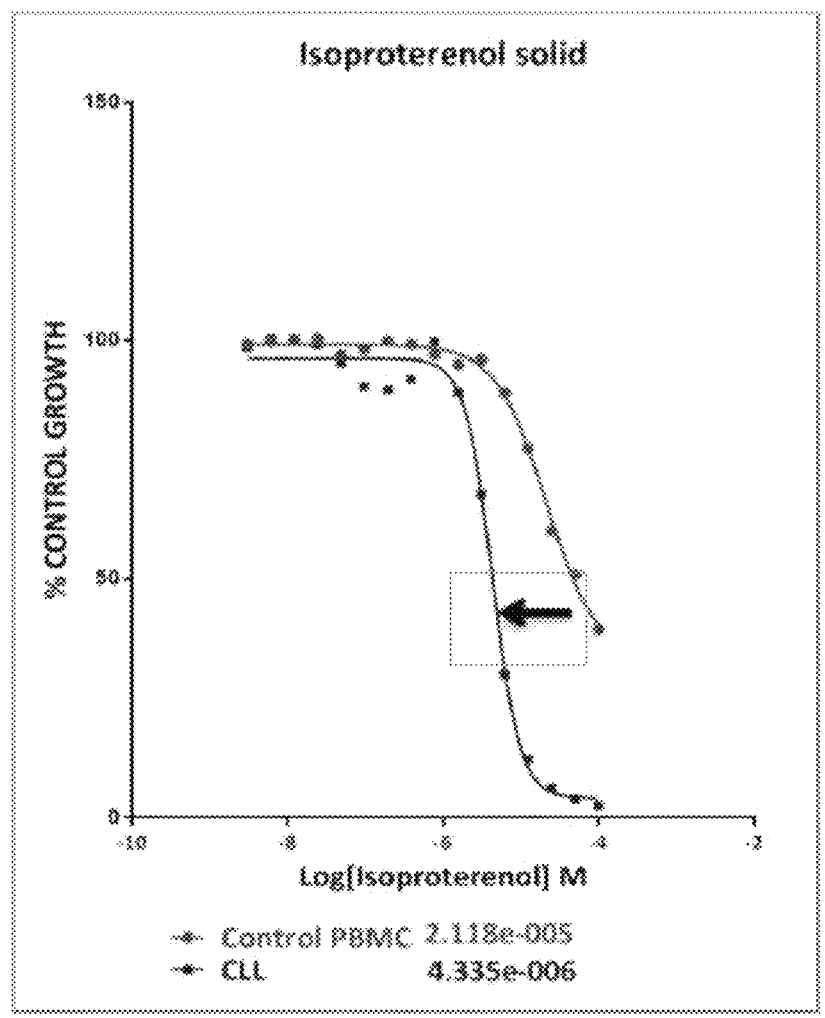
FIG. 1B is a graph depicting the effects of liquid stock isoproterenol on PBMC cells from CLL patients.
Figure 1C:
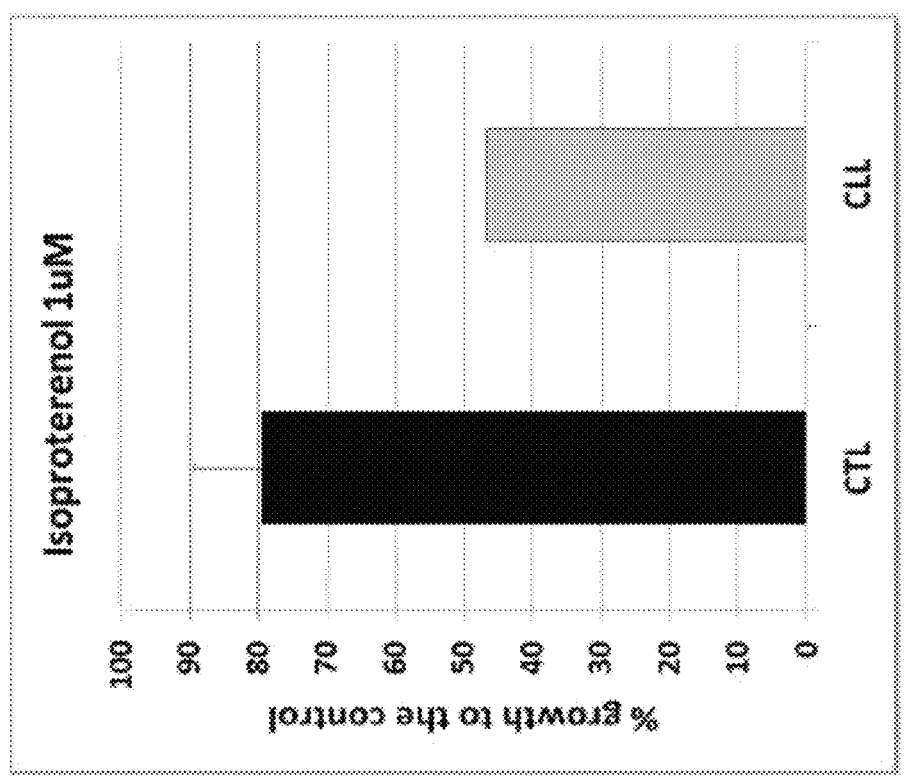
FIG. 1C is a bar graph of efficacy of 1 micromolar isoproterenol on CLL patients.
Figure 1D:
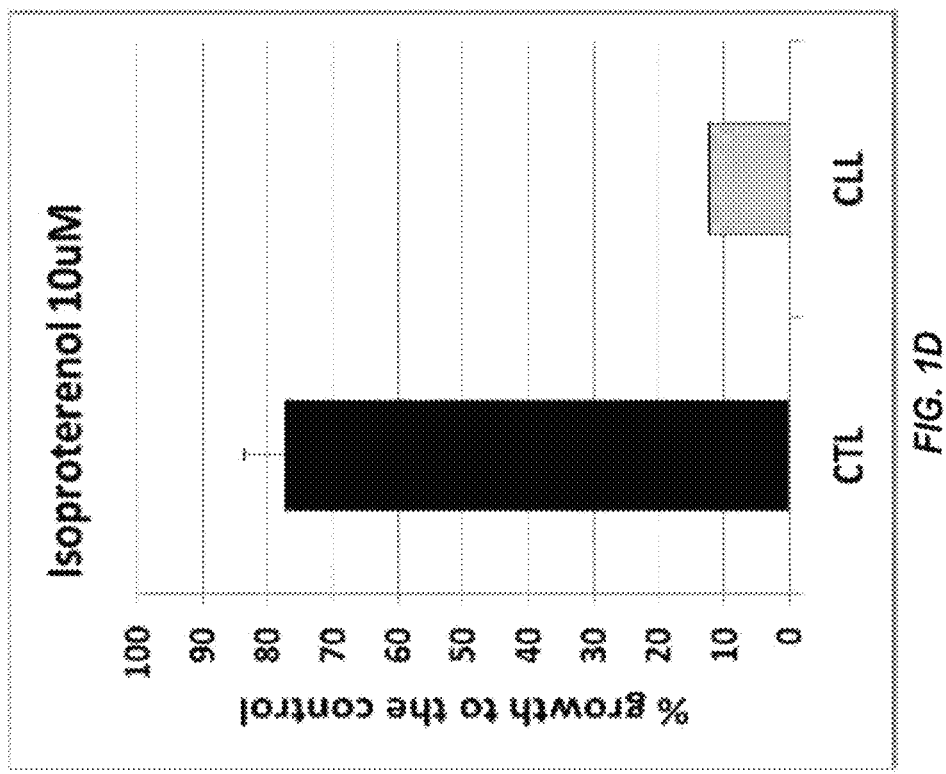
FIG. 1D is a bar graph of efficacy of 10 micromolar isoproterenol on CLL patients.

FIG. 1A-FIG. 1D and FIG. 2A-FIG. 2D depict graphs indicating the effectiveness of isoproterenol against PBMC derived from patient having chronic lymphoid leukemia. The effect of isoproterenol was reproducible when tested from stock solution and primary sample as shown in FIG. 1A-FIG. 1D and FIG. 2A-FIG. 2D. FIG. 1A depicts data of cell growth of PBMC from healthy individuals (Control, CTL) and from chronic lymphoid leukemia (CLL) patients that were incubated with different concentration of isoproterenol prepared from liquid stock. FIG. 1B depicts data of cell growth of PBMC from healthy individuals (Control, CTL) and from chronic lymphoid leukemia (CLL) patients that were incubated with different concentration of isoproterenol prepared from prepared freshly from solid. After 24 hr incubation, the cells viability was measured by TiterGlo assay and the EC50 of growth inhibition was calculated and arrow indicate shift in EC50. FIG. 1C depicts a bar graph of the isoproterenol efficacy in control and CLL plotted as % of growth when isoproterenol was tested at 1 uM from liquid. FIG. 1D depicts a bar graph of the isoproterenol efficacy in control and CLL plotted as % of growth when isoproterenol was tested at 10 uM. The data indicate isoproterenol as potential drug against CLL with and an EC50 4.8 times higher in inducing cell death of PBMC prepared from CLL patients than from control (healthy individuals).

Figure 12A:
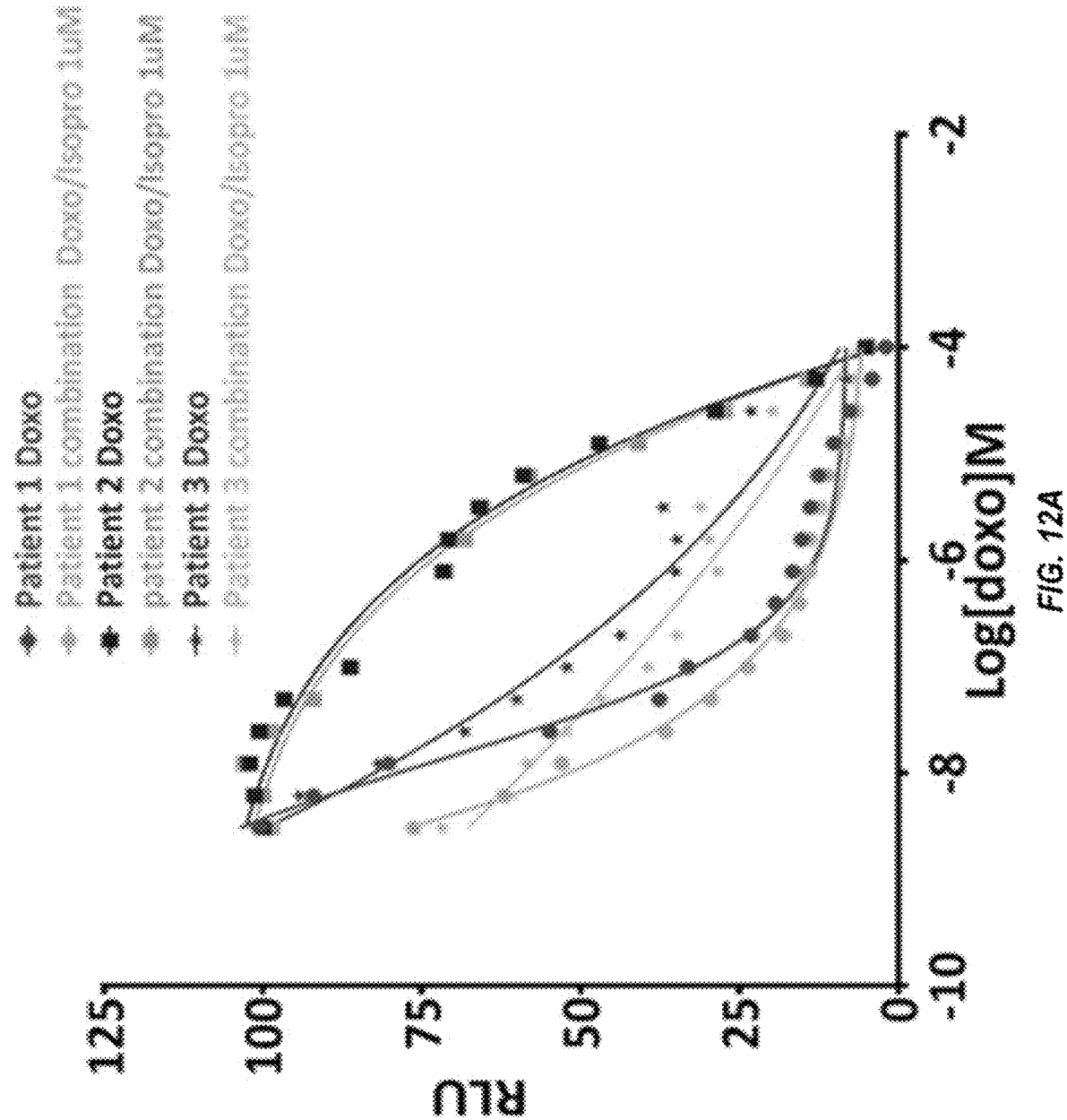
FIG. 12A is a graph depicting the effects of a combination of isoproterenol and doxorubicin on CLL cells from CLL patients.
Figure 12B:
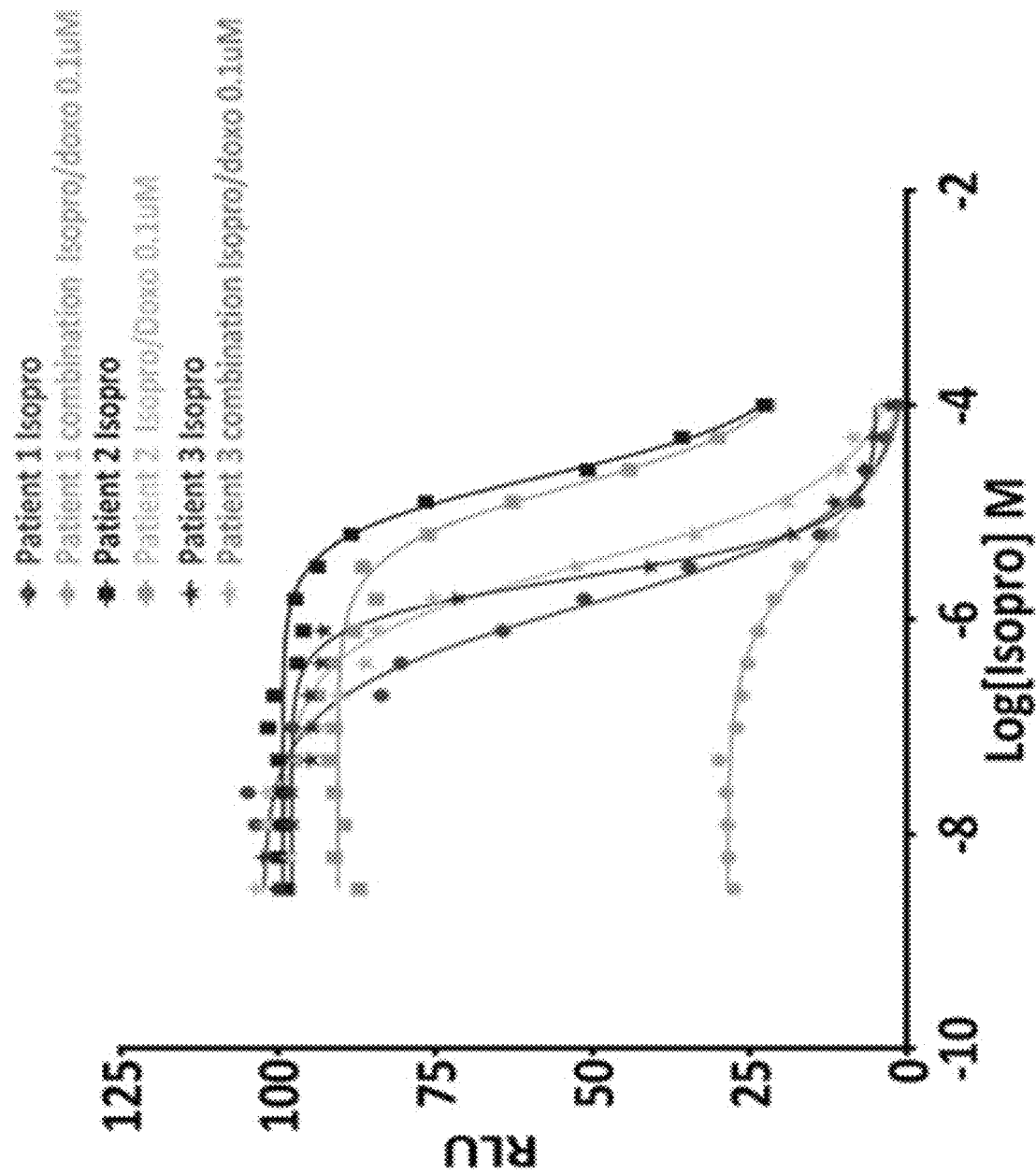
FIG. 12B is a graph depicting the effects of a combination of isoproterenol and doxorubicin on CLL cells from CLL patients.

Isoproterenol was combined with doxorubicin and resulted in enhanced cytotoxic effects in CLL cells from CLL patients (FIGS. 12A-12B). The combination worked well for CLL patients 1 and 3, indicating that the combination could be patient-specific and may have the potential to be developed into personalized medicine. FIG. 12A shows the effect of the isoproterenol/doxorubicin combination which is prepared by varying the concentration of doxorubicin while keeping the concentration of isoproterenol at 1 μM. A solution of doxorubicin was serially diluted in the preparation of the combination. FIG. 12B shows the effect of the isoproterenol/doxorubicin combination which is prepared by varying the concentration of isoproterenol while keeping the concentration of doxorubicin at 0.1 μM. A solution of isoproterenol was serially diluted in the preparation of the combination. The effect of these combinations on CLL cells was tested with the luminescence-based assay, CellTiter-Glo.

Figure 2A:
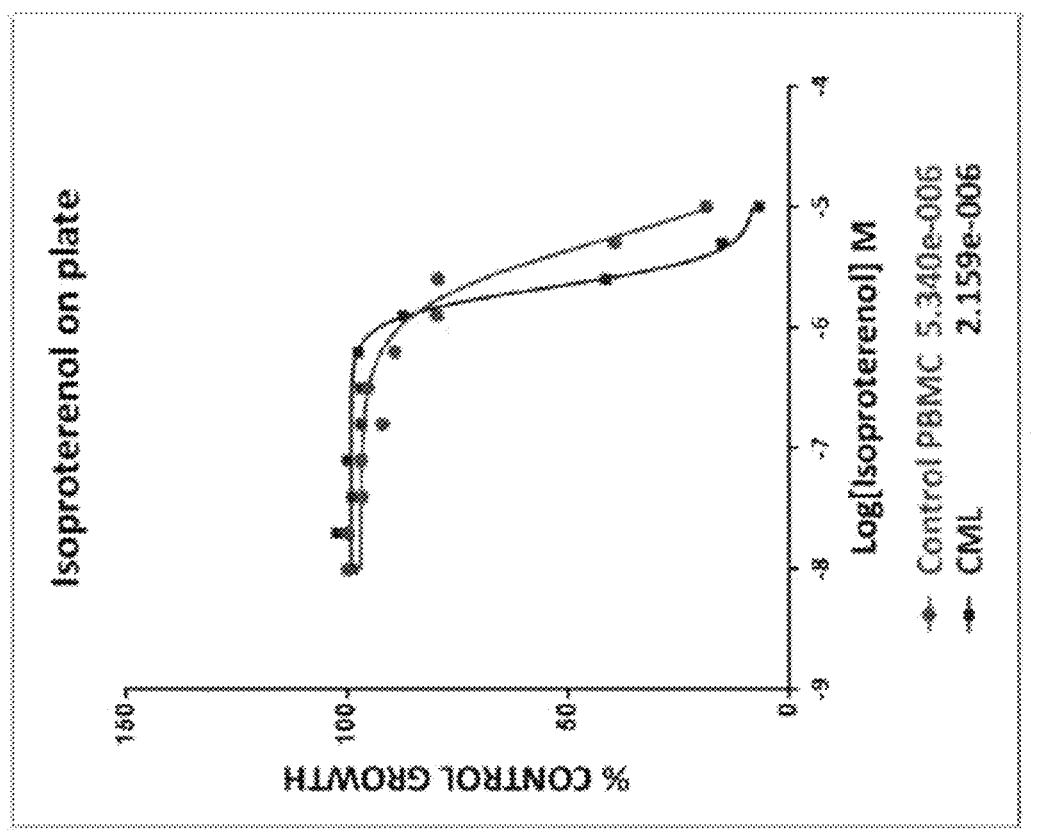
FIG. 2A is a graph depicting the effects of liquid stock isoproterenol on PBMC cells from CML patients.
Figure 2B:
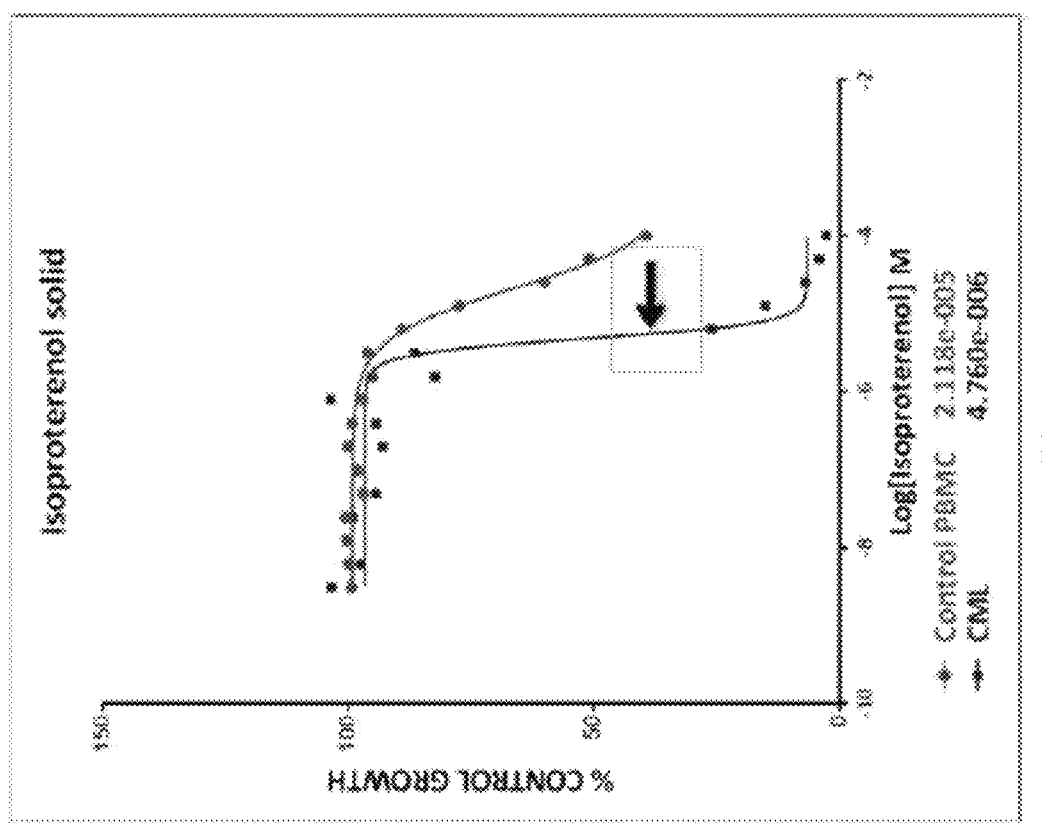
FIG. 2B is a graph depicting the effects of solid isoproterenol on PBMC cells from on CML patients.
Figure 2C:
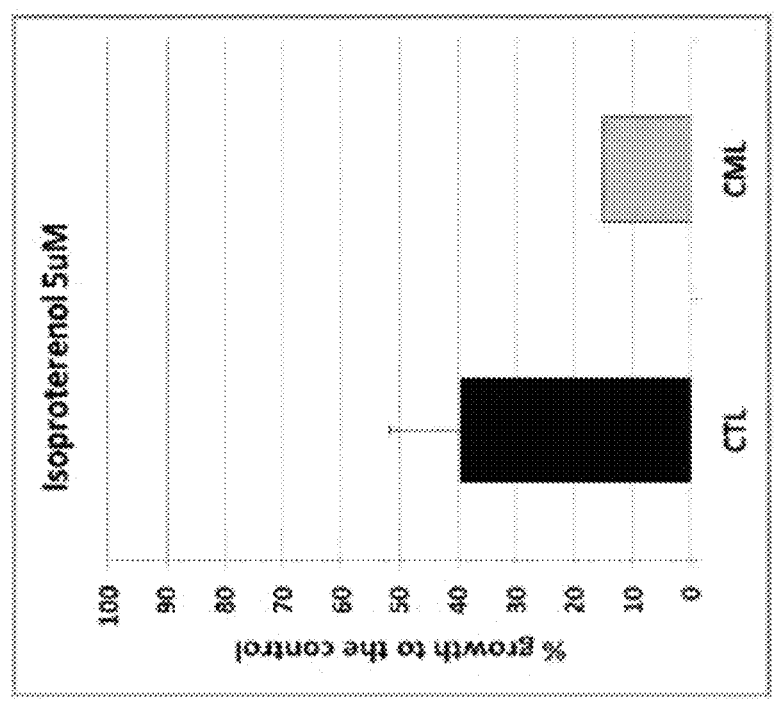
FIG. 2C is a bar graph of efficacy of 5 micromolar isoproterenol on CML patients.
Figure 2D:
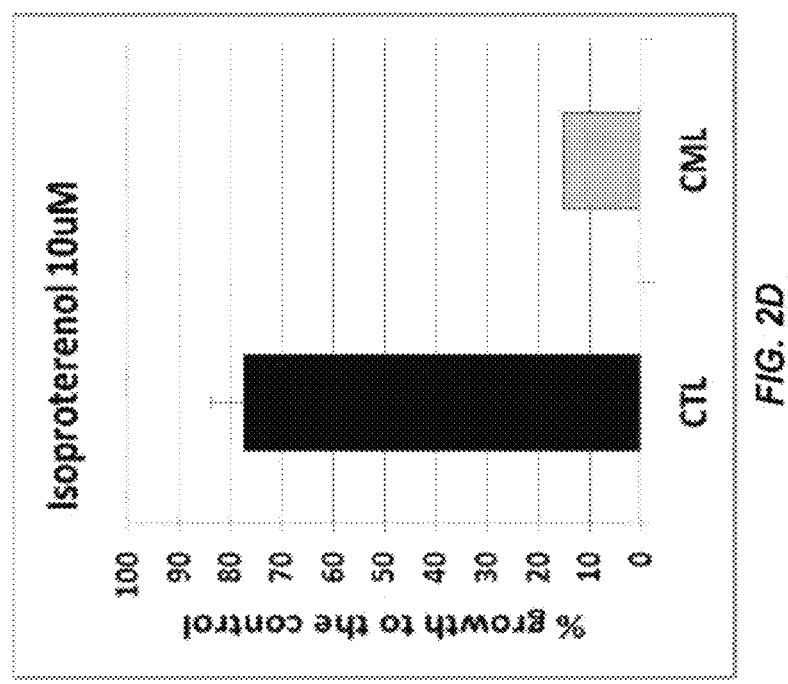
FIG. 2D is a bar graph of efficacy of 10 micromolar isoproterenol on CML patients.

FIG. 2A depicts data of isoproterenol inducing cell death preferentially in chronic myelogenous leukemia (CML) patients' primary PBMC as compared to PBMC from healthy individuals (Control, CTL) when incubated with different concentrations of isoproterenol prepared from liquid stock. FIG. 2B depicts data of isoproterenol inducing cell death preferentially in chronic myelogenous leukemia (CML) patients' primary PBMC as compared to PBMC from healthy individuals (Control, CTL) when incubated with different concentrations of isoproterenol prepared from a solid. After 24 hr incubation, the cells viability was measured by TiterGlo assay and the EC50 of growth inhibition was calculated and arrow indicate shift in EC50. In FIG. 2C a bar graph of the isoproterenol efficacy in control and CML was plotted as % of growth when isoproterenol was tested at 5 uM from liquid. In FIG. 2D a bar graph of the isoproterenol efficacy in control and CML was plotted as % of growth when isoproterenol was tested at 10 uM. Isoproterenol may be a potential drug against CML with and an EC50 4.4 times higher in inducing cell death of PBMC prepared from control (healthy individuals) than PBMC prepared from CML patients.

Isoproterenol is an agonist for the $\beta_1$ and $\beta_2$ adrenoceptor and trace amine-associated receptor 1 (TAAR1) agonist. Interestingly, Methyldopa, sold under the brand name Aldomet among others, is a centrally acting antihypertensive agent is also show an effect on CLL PBMC better than control cell (FIG. 3). Methyldopa is structurally related to Isoproterenol and also an agonist to alpha-2 adrenergic receptors.

FIG. 3A and FIG. 3B depict graphs indicating the effectiveness of methyl dopa against PBMC derived from patient having chronic lymphoid leukemia.

This data indicates that an adrenergic receptor pathway may be involved in the leukemia and targeting this pathway with either antibodies against the adrenergic receptors or other agonist or antagonist may be an approach to develop previously unknown anti-leukemic drugs. It is unclear from the data whether isoproterenol is an agonist or antagonist. Sometimes just binding surface receptors may result in cell proliferation.

FIG. 4A-FIG. 4D depict graphs indicating the effectiveness of olanzapine against PBMC derived from patient having chronic lymphoid leukemia.

Figure 4A:
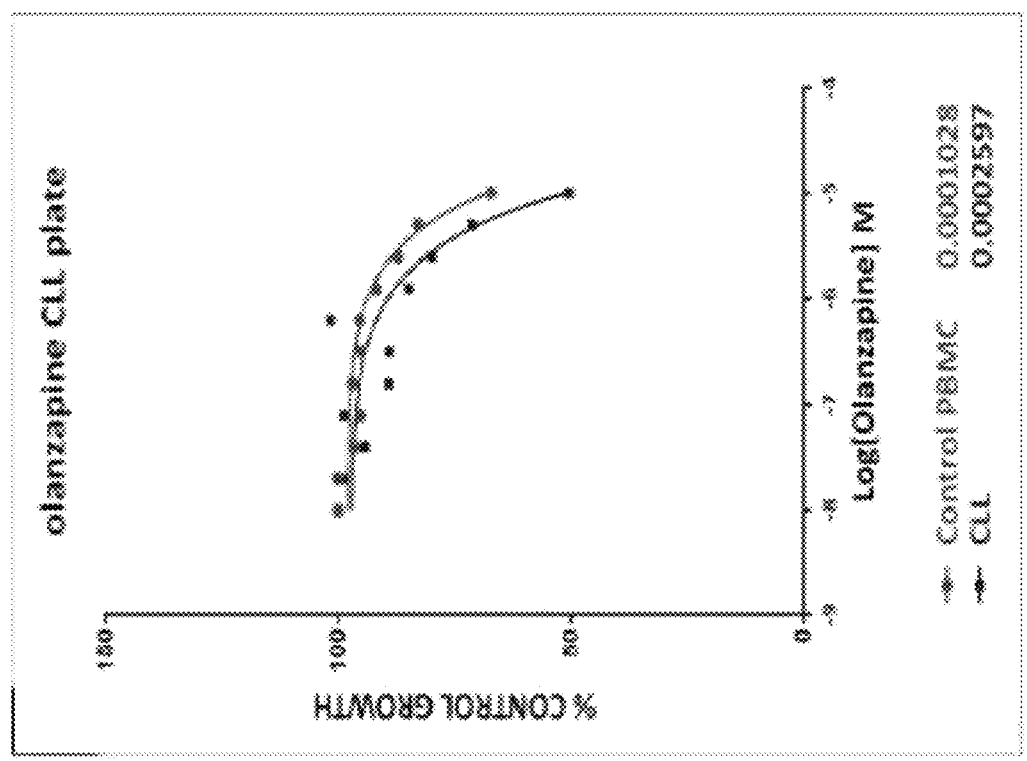
FIG. 4A is a graph depicting the effects of liquid stock olanzapine on PBMC cells from CLL patients and healthy individuals.
Figure 4B:
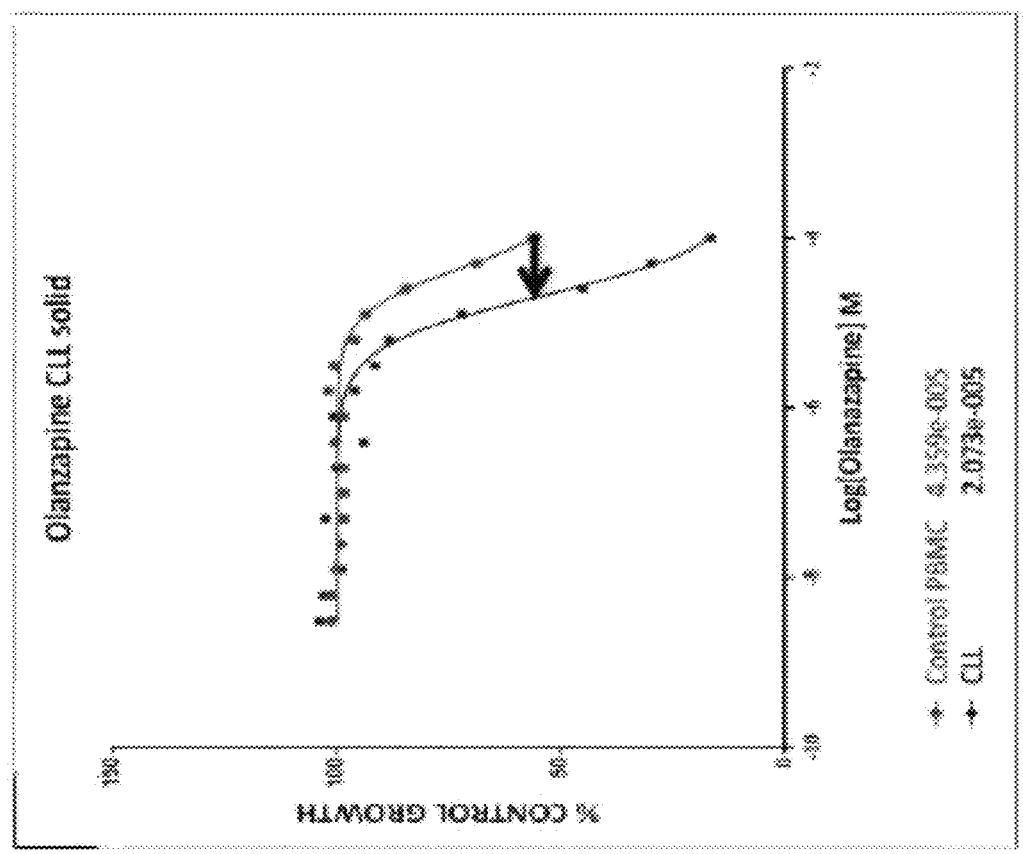
FIG. 4B is a graph depicting the effects of solid olanzapine on PBMC cells from CLL patients and healthy individuals.
Figure 4C:
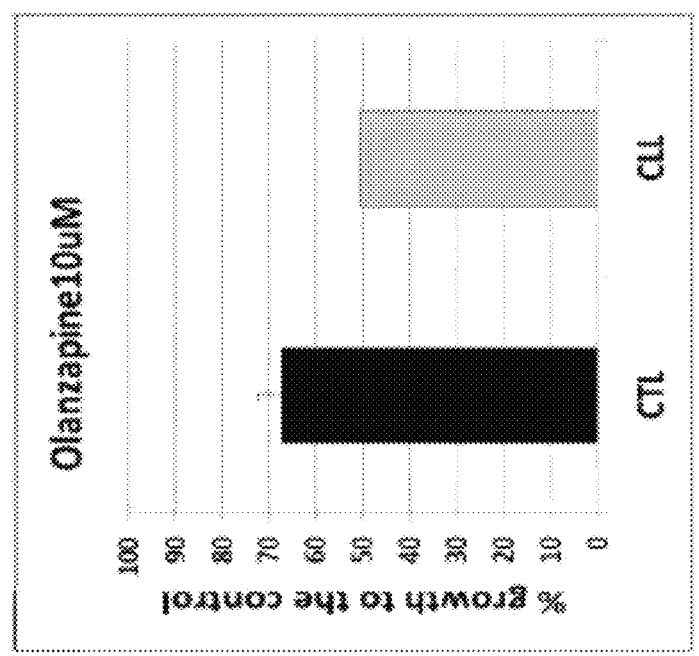
FIG. 4C is a bar graph of efficacy of 10 micromolar olanzapine.
Figure 4D:
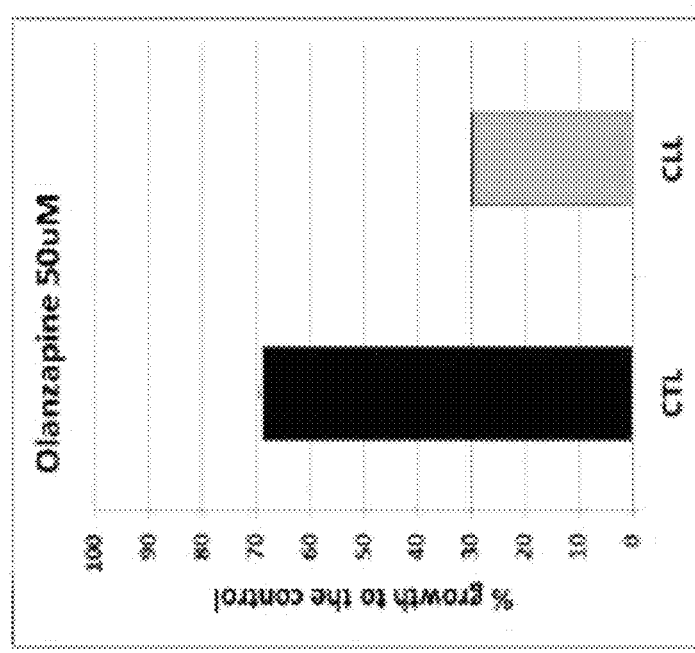
FIG. 4D is a bar graph of efficacy of 50 micromolar olanzapine.

The effect of olanzapine on PBMC is observed on primary cells prepared from patients and the effect is not observed when primary cells are tested after freezing. The freezing of the cells may disrupt or damage receptors that may bind drugs and thus lead to false negative results. The finding indicates that olanzapine and its analogues may be potential treatments for leukemia. The olanzapine targets dopamine D2 and 5-HT receptors, which may be targets to discover and develop leukemic drugs. Anti-dopamine D2 antibody and anti-5-HT receptor antibody may be a viable for treatment for leukemia as components of an antibody-drug conjugate. A possible involvement of dopamine receptor D in leukemia and as potential target has been described in patent reference EP 2680853 A1. The compound efficacy in control and CLL was plotted as % of growth when Olanzapine was tested at 10 uM from liquid (FIG. 4C) and at 50 uM when tested from authentic sample (i.e., fresh solutions prepared with purchased solid Olanzapine before performing the assay) (FIG. 4D).

In addition to isoproterenol and methyldopa, olanzapine, primarily used to treat the depressive episodes of bipolar disorder as well as treatment-resistant depression, also shown to induce cell death in PBMC from CLL patients compared to control cells. Olanzapine is an agonist for dopamine receptor suggesting again that this receptor and/or its pathway could form a target for anti-leukemic drugs.

The invention claimed is:

1. A method for reducing a number of abnormal peripheral blood mononuclear cells (PBMC) that express the Philadelphia chromosome (t9:22 translocation) in a chronic myelogenous leukemia ("CML") patient, the method comprising:
administering an effective amount of isoproterenol to the chronic myelogenous leukemia patient, thereby reducing the number of abnormal PBMC that express the Philadelphia chromosome (t9:22 translocation) in the chronic myelogenous leukemia patient.

2. The method of claim 1, wherein said effective amount is selected to reduce the number of viable abnormal PBMC by 5% to 80% relative to an initial number of abnormal PBMC in the chronic myelogenous leukemia patient prior to administering the effective amount of isoproterenol.

3. The method of claim 1, wherein the effective amount of isoproterenol is in range of 1-100 mg/kg.

4. The method of claim 1, further comprising administering an effective amount of doxorubicin to the chronic myelogenous leukemia patient together with the administering of the effective amount of isoproterenol.

5. The method of claim 4, wherein the effective amount of doxorubicin is in a range of 1-100 mg/kg.

6. The method of claim 1, wherein said abnormal PBMC are buffy coat cells.

7. The method of claim 1, further comprising administering an effective amount of doxorubicin and at least one of methyldopa or olanzapine to the leukemia patient.

8. The method of claim 1, wherein the isoproterenol is conjugated to an antibody selected from the group consisting of an anti-β adrenoceptor antibody and an anti-trace amine-associated receptor 1 antibody.

9. The method of claim 1, wherein the isoproterenol is conjugated via a linker to an antibody selected from the group consisting of an anti-α2 adrenoceptor antibody, an anti-β adrenoceptor antibody, an anti-trace amine-associated receptor 1 antibody, an anti-dopamine receptor antibody, and an anti-serotonin receptor antibody.

10. The method of claim 9, wherein the linker comprises an enzymatically cleavable peptide bond, a hydrolysable bond, or both.

11. The method of claim 8, wherein the isoproterenol is conjugated to an antibody and the conjugate comprises Formula (I):

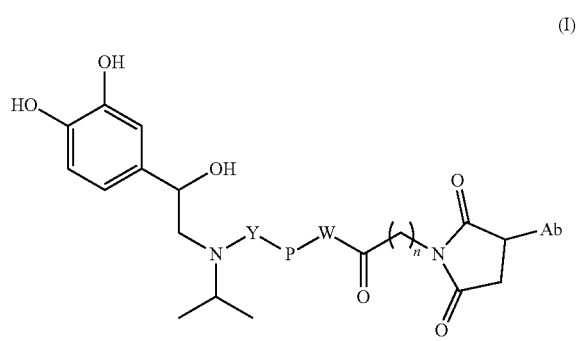

wherein Ab is an antibody selected from the group consisting of an anti-β adrenoceptor antibody and an anti-trace amine-associated receptor 1 antibody; and wherein the linker comprises: Y, which is a self-immolating group bound to the isoproterenol; P, which is a protease sensitive peptide; W, which is a water solubilizing group; and an N-alkyl-succinimide bound to the water solubilizing group and the antibody (Ab), wherein n is 1 to 8.

12. The method of claim 8, wherein the isoproterenol is conjugated to an antibody and the conjugate comprises Formula (III):

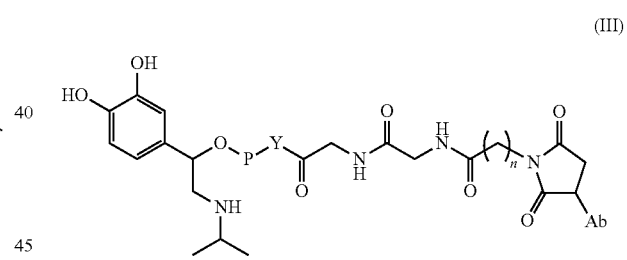

wherein Ab is an antibody selected from the group consisting of an anti-β adrenoceptor antibody and an anti-trace amine-associated receptor 1 antibody; and wherein the linker comprises:
P, which is a pH sensitive group; and
Y, which is a self-immolating group;
a glycine-glycine dipeptide; and
an N-alkyl-succinimide bound to the glycine-glycine peptide and the antibody (Ab), wherein n is 1 to 8.

* * * * *